US006265539B1

(12) United States Patent
Arlinghaus

(10) Patent No.: US 6,265,539 B1
(45) Date of Patent: Jul. 24, 2001

(54) PROPHYLAXIS AND THERAPY OF ACQUIRED IMMUNODEFICIENCY SYNDROME

(75) Inventor: Ralph B. Arlinghaus, Bellaire, TX (US)

(73) Assignee: The University of Texas System The Board of Regents, Austine, TX (US)

( * ) Notice: Subject to any disclaimer, the term of this patent is extended or adjusted under 35 U.S.C. 154(b) by 0 days.

(21) Appl. No.: 07/834,923

(22) Filed: Feb. 13, 1992

Related U.S. Application Data

(60) Division of application No. 07/410,727, filed on Sep. 20, 1989, now Pat. No. 5,128,319, which is a continuation-in-part of application No. 07/090,646, filed on Aug. 28, 1987, now abandoned.

(51) Int. Cl.[7] .......................... A61K 38/00; A61K 38/04; C07K 16/00; C07K 17/00

(52) U.S. Cl. .......................... 530/326; 530/350; 530/327; 424/89

(58) Field of Search .................................... 530/326, 350, 530/327; 424/89

(56) References Cited

U.S. PATENT DOCUMENTS

| | | | |
|---|---|---|---|
| 4,943,628 | 7/1990 | Rosen et al. | 530/326 |
| 4,983,387 | 1/1991 | Goldstein et al. | 424/88 |
| 5,013,548 | 5/1991 | Haynes et al. | 424/89 |
| 5,019,387 | 5/1991 | Haynes et al. | 424/89 |
| 5,030,449 * | 7/1991 | Berzofsky et al. | 530/326 |
| 5,081,226 | 1/1992 | Berzofsky et al. | 530/324 |
| 5,128,319 | 7/1992 | Arlinghaus | 514/12 |
| 5,142,025 | 8/1992 | Putney et al. | 530/350 |
| 5,185,147 | 2/1993 | Papsidero | 424/89 |

FOREIGN PATENT DOCUMENTS

| | | |
|---|---|---|
| 0 267 802 | 5/1988 | (EP) . |
| 0 273 716 | 7/1988 | (EP) . |
| 0 284 587 | 9/1988 | (EP) . |
| 0 433 242 | 6/1991 | (EP) . |
| WO88/05051 | 7/1988 | (WO) . |
| WO 89/03844 | 5/1989 | (WO) . |
| WO 89/07112 | 8/1989 | (WO) . |
| WO 90/00901 | 2/1990 | (WO) . |
| WO91/01996 | 2/1991 | (WO) . |
| WO 91/04051 | 4/1991 | (WO) . |
| WO91/09869 | 7/1991 | (WO) . |
| WO91/13910 | 9/1991 | (WO) . |
| WO92/21377 | 12/1992 | (WO) . |
| WO93/04697 | 3/1993 | (WO) . |
| WO93/15750 | 8/1993 | (WO) . |
| WO93/18055 | 9/1993 | (WO) . |
| WO93/21218 | 10/1993 | (WO) . |
| WO94/00488 | 1/1994 | (WO) . |

OTHER PUBLICATIONS

Modrow, et al., 1987, Computer–Assisted Analysis of . . . J. of Virology 61(2): 570–578.*

Wain–Hobson, 1985, "Nucleotide Sequence of the AIDS Virus, LAV", Cell 40: 9–17.*

Ghiara et al., "Crystal Structure of the Principal Neutralization Site of HIV–1," *Science,* 264:82–85, 1994.

Schild et al., "Efficiency of Peptides and Lipopeptides for in vivo Priming of Virus–Specific Cytotoxic T Cells," *Eur. J. Immunol.,* 21:2649–2654, 1991.

Maddox, J., "AIDS Research Turned Upside Down," *Nature,* 353:297, 1991.

Anderson, C., "Department of Energy Faces Hard Choices," *Nature,* 353:287, 1991.

Kion, T. and Hoffmann, G., "Anti–HIV and Anti–MHC Antibodies in Alloimmune and Autoimmune Mice," *Science,* 253:1138–1140, 1991.

Kaneshima et al., "Human Immunodeficiency Virus Infection of Human Lymph Nodes in the SCID–hu Mouse," *Proc. Natl. Acad. Sci. USA,* 88:4523–4527, 1991.

Clerici et al., "Detection of Cytotoxic T Lymphocytes Specific for Synthetic Peptides of gp160 in HIV–Seropositive Individuals," *J. Immunol.,* 146(7):2214–2219, 1991.

Freed et al., "Identification of the Principal Neutralizing Determinant of Human Immunodeficiency Virus Type 1 as a Fusion Domain," *J. Virol.,* 65(1):190–194, 1991.

Freed & Risser, "Identification of Conserved Residues in the Human Immunodeficiency Virus Type 1 Principal Neutralizing Determinant That Are Involved in Fusion," *AIDS Res. Human Retroviruses,* 7(10):807–811, 1991.

Murakami et al., "A Principal Neutralizing Domain of Human Immunodeficiency Virus Type 1 Interacts with Proteinase–Like Molecule(s) at the surface of Molt–4 Clone 8 Cells," *BBA,* 1079:279–284, 1991.

Berzofsky et al., "Development of Artificial Vaccines Against HIV Using Defined Epitopes," *FASEB J.,* 5:2412–1418, 1991.

(List continued on next page.)

*Primary Examiner*—James Housel
*Assistant Examiner*—Bratt Nelson
(74) *Attorney, Agent, or Firm*—Fulbright & Jawors

(57) ABSTRACT

An active peptide consisting essentially of 7 to about 30 residue and having a sequence that corresponds to a conserved domain of an HIV protein is disclosed, as is a multimer containing that peptide, an aqueous composition containing the multimer and methods of using and making the same. The aqueous composition containing an immunologically effective amount of an active peptide multimer, when introduced into an immunocompetent host animal in an immunologically effective amount, is capable of inducing cellular immunity against the native HIV protein to which the active peptide of the multimer corresponds in sequence, but is not capable of inducing production of antibodies that immunoreact with that native HIV protein.

18 Claims, 11 Drawing Sheets

OTHER PUBLICATIONS

Aichele et al., "Antiviral Cytotoxic T Cell Response Induced by in Vivo Priming with a Free Synthetic Peptide," *J. Exp. Med.,* 171:1815–1820, 1990.

Hosmalin et al., "An Epitope in Human Immunodeficiency Virus 1 Reverse Transcriptase Recognized by Both Mouse and Human Cytotoxic T Lymphocytes," *PNAS,* 87:2344–2348, 1990.

Sastry & Arlinghaus, "A Novel HIV Vaccine Strategy," *Hematologic Pathology,* 4(3):157–159, 1990.

Takahashi et al., "Induction of Broadly Cross–Reactive Cytotoxic T Cells Recognizing an HIV–1 Envelope Determinant," *Science,* 255:333–336, 1992. Published in USA.

Rénia et al., "In Vitro Activity of $CD4^+$ and $CD8^+$ T Lymphocytes from Mice Immunized with a Synthetic Malaria Peptide," *Proc. Natl. Acad. Sci. USA,* 88:7963–7967, 1991. Published in USA.

Hart et al., "Priming of Anti–Human Immunodeficiency Virus (HIV) $CD8^+$ Cytotoxic T Cells In Vivo by Carrier–Free HIV Synthetic Peptides," *Proc. Natl. Acad. Sci. USA,* 88:9448–9452, 1991. Published in USA.

Gao et al., "Priming of Influenza Virus–Specific Cytotoxic T Lymphocytes Vivo by Short Synthetic Peptides," *J. Immunol.,* 147(10):3268–3273, 1991. Published in USA.

Schjulz et al., "Peptide–Induced Antiviral Protection by Cytotoxic T Cells," *Proc. Natl. Acad. Sci. USA,* 88:991–993, 1991. Published in USA.

Sette et al., "A Microcomputer Program for Hydrophilicity and Amphipathicity Analysis of Protein Antigens," *Molec. Immunol.,* 23(8):807–810. 1986.

Coates et al., "AIDS Vaccine Predictions," *Nature,* 326:549–550, 1987.

Margalit et al., "Prediction of Immunodominant Helper T cell Antigenic Sites from the Primary Sequence," *J. Immunol.,* 138(7):2213–2229, 1987. Published in USA.

DeLisi, C. and J. Berzofsky, "T–cell Antigenic Sites Tend to be Amphipathic Structures," *Proc. Natl. Acad. Sci. USA,* 82:7048–7052, 1985. Published in USA.

Sastry & Arlinghaus, "Identification of T–Cell Epitopes Without B–Cell Activity in the First and Second Conserved Regions of the HIV Env Protein," *Current Science,* 5(6):699–707, 1991.

Lasarte et al., "Induction of Cytotoxic T Lymphocytes in Mice Against the Principal Neutralizing Domain of HIV–1 by Immunization with An Engineered T–Cytotoxic–T–Helper Synthetic Peptide Construct," *Cellular Immunology,* 141:211–218, 1992.

Cohen, "AIDS Research Shifts to Immunity," *Science,* 257:152–154, 1992.

Sastry et al., "Rapid in Vivo Induction of HIV–Specific $CD8^+$ Cytotoxic T Lymphocytes by a 15–Amino Acid Unmodified Free Peptide from the Immunodominant V3–Loop of GP120," *Virology,* 188:502–509, 1992.

Berzofsky et al., "Epitopes of HIV and SIV. I. Host Responses," *Aids Res. Hum. Retroviruses,* 7(2):144, 1991.

Dadaglio et al., "Epitope Recognition of Conserved HIV Envelope Sequences by Human Cytotoxic T Lymphocytes," *J. Immunol.,* 147(7):2302–2309, 1991.

Kemp et al., "Diagnostic and Antiviral Applicaitons of Synthetic HIV–1 Peptides," *In Peptides: Chemistry, Structure and Biology,* Proceedings of the Eleventh American Peptide Symposium, Jean E. Rivier and Garland R. Marshall, Eds., Jul. 9–14, 1989, La Jolla, CA.

Kloetzer et al., "Peptides of Feline Leukemia Virus Protein p15 E as Immunosuppressants and Vaccines," *Chemical Abstracts,* Abstract No. 9042x; 111:82, 1989, regarding WO 88/05,783, Ortho Pharmaceutical Corp.

McMichael et al., "Peptide Fragments of Human Immunodeficiency Virus (HIV) for Stimulation of Cytotoxic T–Cell Immunity," *Chemical Absracts,* Abstract No. 215075v, 112:487, 1990, regarding EP 346,022, Medical Research Counsel.

Shinnick et al., "Synthetic Polypeptides, Antibodies, Diagnostic Systems, and Kits for Immunological Detection of Infections with Tuberculosis Mycobacteria," *Chemical Abstracts,* Abstract No. 36241s, 108:496, 1988, regarding WO 87/01,118, Scripps Clinic and Research Foundation.

Takahashi et al., "A Single Amino Acid Interchange Yields Reciprocal CTL Specificities for HIV–1 gp160," *Science,* 246:118–121, 1989.

Supplementary European Search Report dated Aug. 19, 1992.

PCT Search Report dated Mar. 29, 1993.

Clark, William R., *The Experimental Foundations of Modern Immunology,* John Wiley & Sons, publishers, pp. 278–283, 1980.

Coates, et al., 1987, "AIDS Vaccine Predictions", Nature 326: 549–550.*

Modrow, et al., 1987, Computer–Assisted Analysis of .... J. Virology 61(2): 570–578.*

Wain–Hobson, 1985, "Nucleotide Sequence of the AIDS Virus, LAV", Cell 40:9–17.*

Margalit, et al., 1987, "Prediction of ...." J. of Immunol., 138: 2213–2229.*

DeLisi et al., 1985, PNAS 82: 7048–7052.*

Sette, et al., 1986, Molecular Immunology 23:807–810.*

* cited by examiner

PROPHYLAXIS AND THERAPY OF ACQUIRED IMMUNODEFICIENCY SYNDROME

CROSS-REFERENCE TO RELATED APPLICATION

This application is a division of application Ser. No. 07/410,727 filed Sep. 20, 1989 now U.S. Pat. No. 5,128,319, which was a continuation-in-part of Ser. No. 07/090,646, filed Aug. 28, 1987, now abandoned.

FIELD OF THE INVENTION

The present invention concerns a method to prevent or treat acquired immunodeficiency syndrome (AIDS) and involves a new and novel approach for making an immunizing composition or inoculum. The inoculum or composition comprises synthetic peptide multimer that exhibits certain T cell activating immunological characteristics of one or more proteins encoded by the viral causative agent of this disease.

BACKGROUND OF THE INVENTION

AIDS was first recognized in the United States in 1981; the number of cases has been increasing at a dramatic pace since then. Since 1978 more than 2.4 million AIDS infections have been reported in the United States, alone (Rees, Nature, 326:343, 1987). Once significant immunosuppressive symptoms appear in an infected individual, the expected outcome of the infection is death. There is currently no known treatment that can indefinitely delay or prevent the fatal consequences of the disease. Although the disease first manifested itself in homosexual or bisexual males and intravenous drug abusers, it has now spread to others by means such as intimate sexual contact with or receipt of blood products from a carrier of the virus.

The causative agent, associated with AIDS has been identified as a group of closely related retroviruses commonly known as Human T Cell Lymphotrophic Virus-type III (HTLV-III), Lymphadenopathy Viruses (LAV), AIDS-Related Viruses (ARV), or more recently named Human Immunodeficiency Virus (HIV). These viruses will be collectively referred to herein for convenience as HIV.

Like other retroviruses, HIV has RNA as its genetic material. When the virus enters the host cell, a viral enzyme known as reverse transcriptase copies the viral RNA into a double stranded DNA. The viral DNA migrates to the nucleus of the cell where it serves as a template for additional copies of viral RNA which can then be assembled into new viral particles. The viral RNA can also serve as messenger RNA for certain viral proteins [either the viral core proteins (known as p18, p24 and p13)] or the reverse transcriptase, or be "spliced" into specific viral messenger RNAs necessary to produce several other viral proteins including two glycosylated structural proteins known as gp41 and gp120 which are inserted in the outer membrane of the virus (Wain-Hobson et al., Cell 40:9, 1985). A recent study has shown that purified gp120 induces antibody in the goat, horse and rhesus monkey that neutralizes HIV in lab tests (Robey et al., Proc. Natl. Acad. Sci., USA 83:7023, 1986).

Vaccines have been used for many years to prevent infections caused by agents such as viruses. The general approach has been to inject healthy individuals with, for example, a killed or modified virus preparation in order to prime the individual's immune systems to mount an assault on the infecting virus. Recent advances in recombinant DNA technology have allowed safer methods of vaccination that involve use of exposed viral components produced by microbial systems. After sufficient purification, the viral component, for example a protein subunit, is administered as a vaccine in a suitable vehicle and/or an adjuvant. The latter stimulates the host's system in a way that improves the immune response to the viral subunit.

Another potential method of making a vaccine is by using chemically synthesized peptide fragments of a viral protein subunit. This method has several advantages over the other methods of producing vaccines, including purity of the product, reproducibility and specificity of the immune response.

Surface antigens of an infecting virus can elicit T cell and B cell responses. From the work of Milich and coworkers (Milich et al., J. Exp. Med. 164:532, 1986; Milich and McLachlan, Science, 232:1398, 1986) it is clear that some regions of a protein's peptide chain can possess either T cell or B cell epitopes. These epitopes are frequently distinct from each other and can comprise different peptide sequences. Other examples include the work of Maizel et al., (Eur. J. Immunol. 10:509, 1980) for hen egg-white lysozyme, and Senyk et al., (J. Exp. Med., 133:1294, 1971) for glucagon. Thus, short stretches of a protein sequence can elicit a T cell response but not a B cell response. A more complete review of these and other observations pertinent to this point is included in the work of Livingstone and Fathman (Ann. Rev. Immunol., 5:477, 1987).

A short peptide region within the surface protein of infectious Hepatitis B virus has been shown to elicit only a T cell response in mice (Milich et al., 1986). Specifically, a synthetic peptide, whose sequence is derived from amino acids numbered 120–132 located within the pre-S(2) domain of the Hepatitis B surface antigen gene, elicited a very strong T cell priming response to the peptide but stimulated only a very weak antibody response. In other words, mice mounted a poor antibody response to that peptide, but the T cells of immunized mice were efficiently primed (i.e. activated) to recognize that peptide as measured in T cell proliferation assays (Milich et al., 1986). The low level of the antibody produced by mice immunized with this peptide did not bind to the native viral surface antigen. The sequence of this T cell active peptide is:

Amino terminal-MQWNSTTFHQTLQ-carboxy-terminal. The single letter code for amino acids used throughout this application is: A, alanine; C cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; and Y, tyrosine.

In contrast to the above-described results, a second peptide sequence (amino acids 132–145) elicited a very weak T-cell response in mice (Milich et al., 1986). This second peptide did, however, efficiently bind antibody raised against it under conditions where a T cell epitope is provided.

The sequence of the second or B cell active peptide is:

Amino terminal-DPRVRGLYFPAGG-carboxy-terminal. Mice were also immunized with a longer peptide made up of both of the above-mentioned T- and B-active peptide sequences. In this case, high titers of antibody were produced against the B site peptide but not the T site peptide. The combination of both T- and B-sites within one peptide should stimulate both T and B cell responses, as measured by producing a specific antibody to the B cell epitope of the peptide chain. Synthetic peptide antigens may be constructed to produce two types of immune responses: T-cell only and T cell combined with a B cell response.

Cellular immune responses provide a major mechanism for reducing the growth of virus-infected cells (Doherty et al., Adv. Cancer Res., 42:1, 1985). A report by Earl et al., (Science, 234:728, 1986) demonstrated T-lymphocyte priming and protection against the Friend virus (a retrovirus)-induced mouse leukemia by a viral surface protein vaccine. Direct evidence for the role of a subset of T-lymphocytes (OKT8/LEU2 positive) in suppressing HIV growth in vitro was recently obtained by Walker et al., (Science, 234:1563, 1986). This study further demonstrated that, after depletion of $CD8^+$ T-lymphocytes from the blood of HIV-infected individuals, large quantities of HIV were isolated from peripheral blood mononuclear cells of four of seven asymptomatic, seropositive homosexual men who were initially virus-negative or had very low levels of virus. Thus, the $CD8^+$ subset of T-lymphocytes may play a role in virus infected individuals to prevent HIV replication and disease progression.

SUMMARY OF THE INVENTION

The present invention contemplates a peptide, a peptide multimer, an aqueous composition containing the peptide multimer and a method of using the composition.

A peptide of the invention contains 7 to about 30 amino acid residues, and has a sequence that corresponds to a conserved domain of an HIV protein such as the gp160 envelope and core proteins. Preferred peptides have a sequence that corresponds to a portion of a conserved domain selected from the group consisting of the first, second, third and fifth conserved domains of the gp160 molecule.

A peptide of the invention is generally used as a portion of a peptide multimer. Two specific classes of peptide multimers are disclosed. In one class, the amino-terminal residue of a peptide is peptide-bonded to a spacer peptide that contains an amino-terminal lysyl residue and one to about five amino acid residues such as glycyl residues to form a composite polypeptide. Those added residues of the spacer peptide do not interfere with the immunizing capacity of the multimer, nor with its capacity to form surfactant-like micelles in aqueous compositions. The alpha- and epsilon-amino groups of the amino-terminal lysyl residue are amidified with a $C_{12}$–$C_{18}$ fatty acid such as palmitic acid to form the reaction product that is used. The di-amide so formed forms surfactant-like micellular multimers in an aqueous composition.

A second class of multimer is a polymer having a before-described peptide as a repeating unit. Here, each peptide is synthesized to contain a cysteine (Cys) residue at each of its amino- and carboxy-termini. The resulting di-cysteine-terminated (di-Cys) peptide is then oxidized to polymerize the di-Cys peptide monomers into a polymer or cyclic peptide multimer in which the peptide repeating units are linked by stine (oxidized cysteine) residues.

A peptide multimer of either class can contain one or a plurality of different peptide sequences. A before-described peptide of a multimer is an "active" peptide in that when used in a composition discussed below, the multimer can induce cell mediated immunity such as production of cytotoxic T cells. A multimer can also include an inactive peptide, for example to assist in dispersing the multimer in the aqueous medium. The lysyl-containing peptide spacer discussed before can be viewed as such an inactive peptide.

The peptide multimer is utilized in an aqueous composition (inoculum). That composition contains water having a before-described multimer dispersed therein. The composition, when used to immunize an immunocompetent host animal such as a mouse, has the capacity of inducing cell mediated immunity such as cytotoxic T cell activation to the native HIV protein corresponding in sequence to that of an active peptide of the multimer, but does not substantially induce production of antibodies that immunoreact with that corresponding native HIV protein. The composition thus contains an immunizing effective amount of a before-discussed multimeric peptide.

In one method aspect of the invention, an immunizing amount of an above composition containing an immunizing effective amount of an active peptide multimer is introduced into (administered to) an animal host such as a mouse or human to induce cellular immunity such as T cell immunity to a preselected native HIV protein without production of antibodies that immunoreact with that preselected native HIV protein. The preselected HIV protein is the HIV protein to which the active peptide corresponds in sequence. The immunized animal is then maintained to permit the immunity to be induced. This immunization can be repeated or boosted as desired.

Another method aspect of this invention is a method of killing target cells that exhibit an HIV protein or a portion of an HIV protein on the cell surfaces. Here, target cells that exhibit an HIV protein or a portion of an HIV protein on their cell surfaces such as HIV-infected T cells or leukocytes that are artificially made to express cell surface HIV proteins are contacted with a killing effective amount of cytotoxic T cells that have been activated using a before-described composition. The cell surface-exhibited HIV protein and the HIV protein to which an active peptide of the multimer corresponds in sequence are the same proteins, since the core protein and the two processed portions of the gp160 protein (the gp120 and gp41 envelope proteins) are the proteins normally found on HIV-infected cell surfaces. That contact is maintained for a time period sufficient for the cytotoxic T cells to kill the target cells. This method can be carried out in vitro or in viva in the body of a host animal.

BRIEF DESCRIPTION OF THE DRAWINGS

In the drawings forming a portion of this disclosure.

DESCRIPTION OF THE PREFERRED EMBODIMENT

A. Overview

Figure 1:
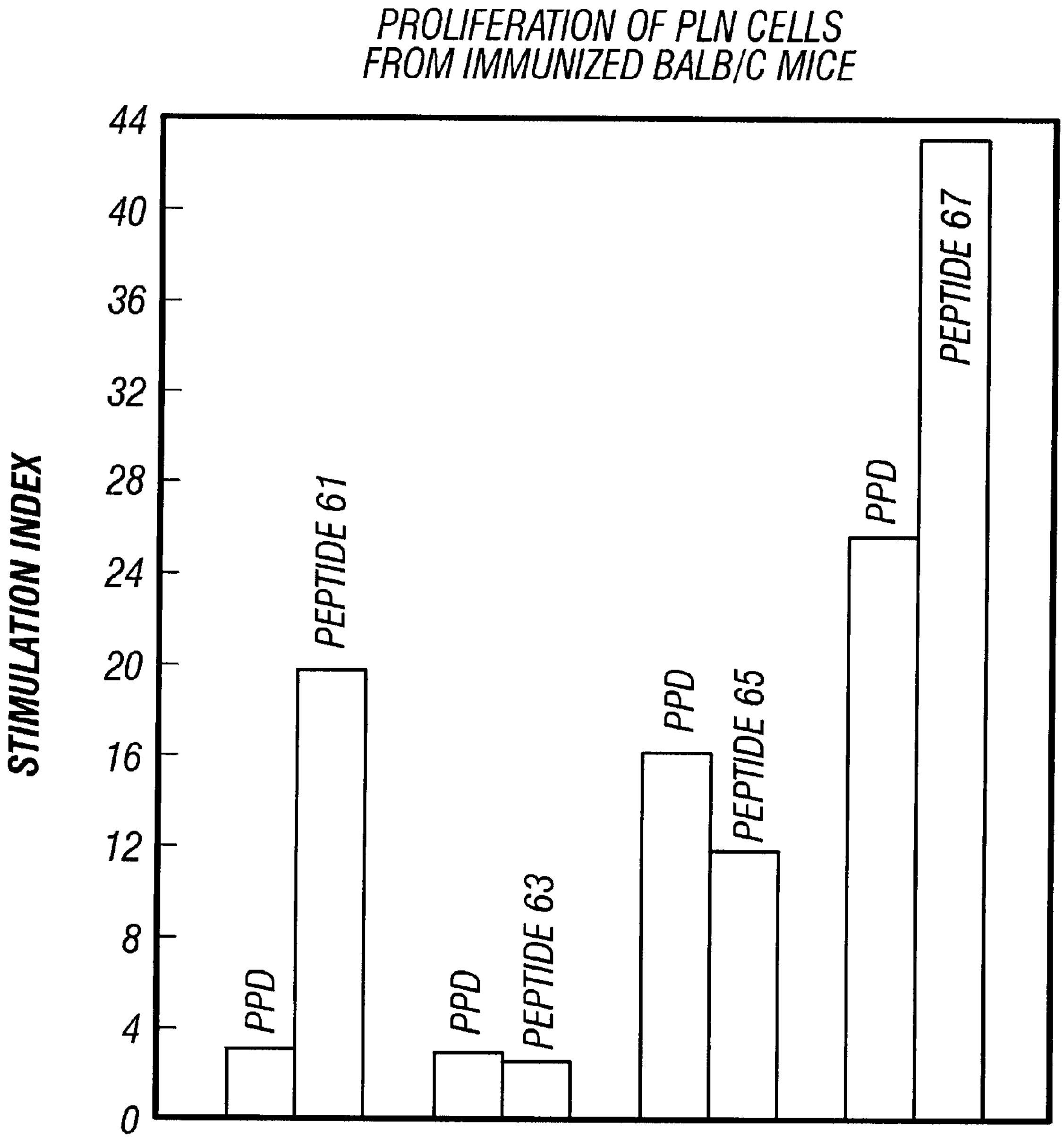
FIG. 1 is a graph that illustrates the in vitro proliferation of popliteal lymph node (PLN) cells after in vivo immunization of Balb/c mice with an aqueous composition containing an immunologically effective amount of a peptide multimer polymer of this invention prepared from each of peptides 61, 63, 65 and 67. Tuberculin purified protein derivative (PPD) was used as a control, as shown. A $^{3}$H-thymidine ($^{3}$H-TdR) incorporation assay was used for these studies. The data are illustrated as a stimulation index, which is calculated as the fold increase in radioactivity counts in the presence of the peptide multimer antigen compared to background values where no antigen was added. Details of this study are discussed hereinafter.
Figure 2:
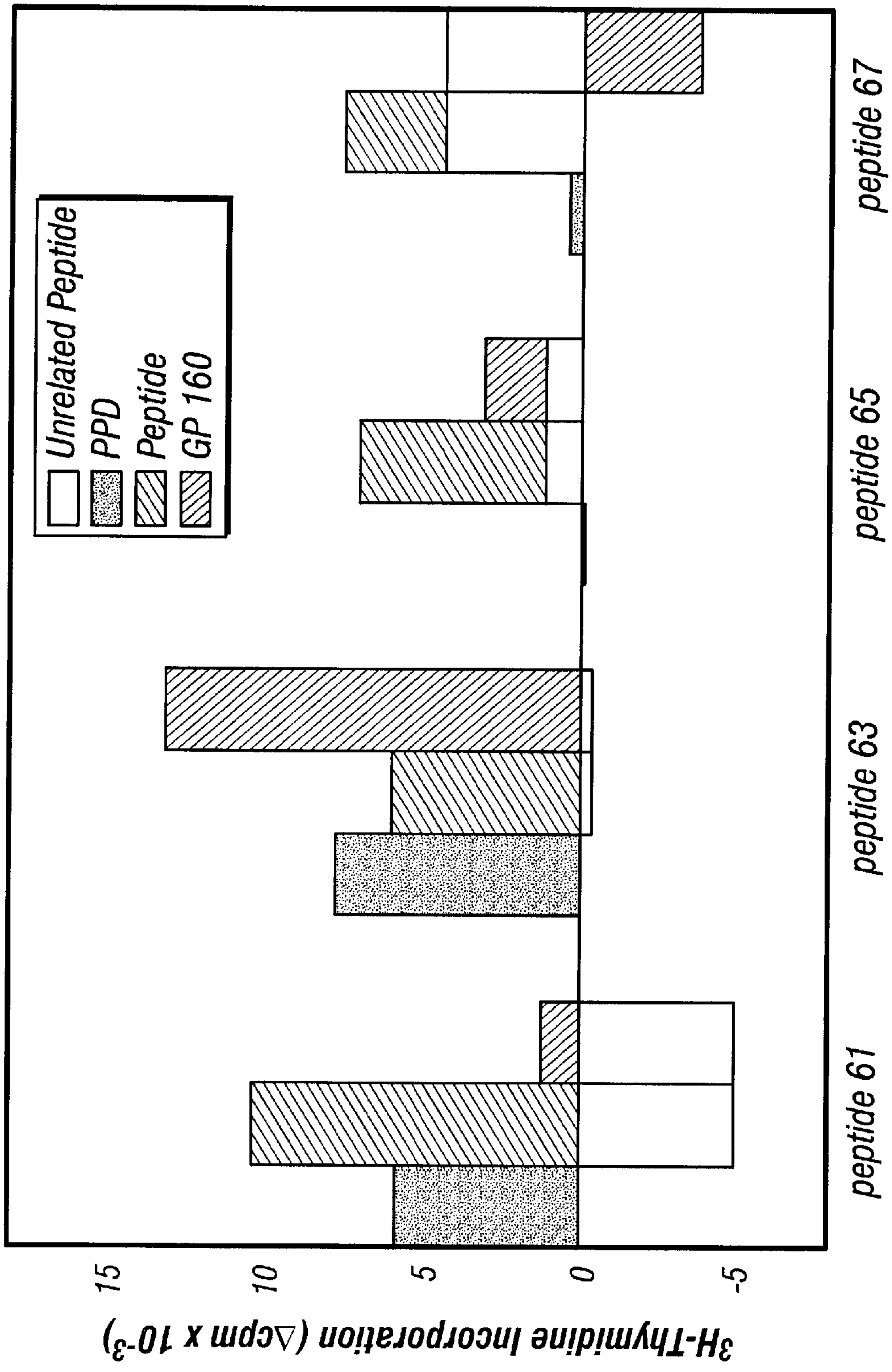
FIG. 2 is a graph that illustrates $^{3}$H-TDR incorporation (T cell proliferation) of PLN cells after immunization of B6C3 F1 mice with an aqueous composition containing an immunologically effective amount of a peptide multimer polymer of this invention prepared from each of peptides 61, 63, 65 and 67. An unrelated peptide, PPD and gp160 were used as controls. The data are shown as the $^{3}$H-TdR incorporation [delta (Δ) counts per minute (cpm)] obtained by subtracting radioactivity values in control wells without added antigen from those in wells with antigen. Details of this study and those of the studies of FIGS. 3–5 are discussed hereinafter.
Figure 3:
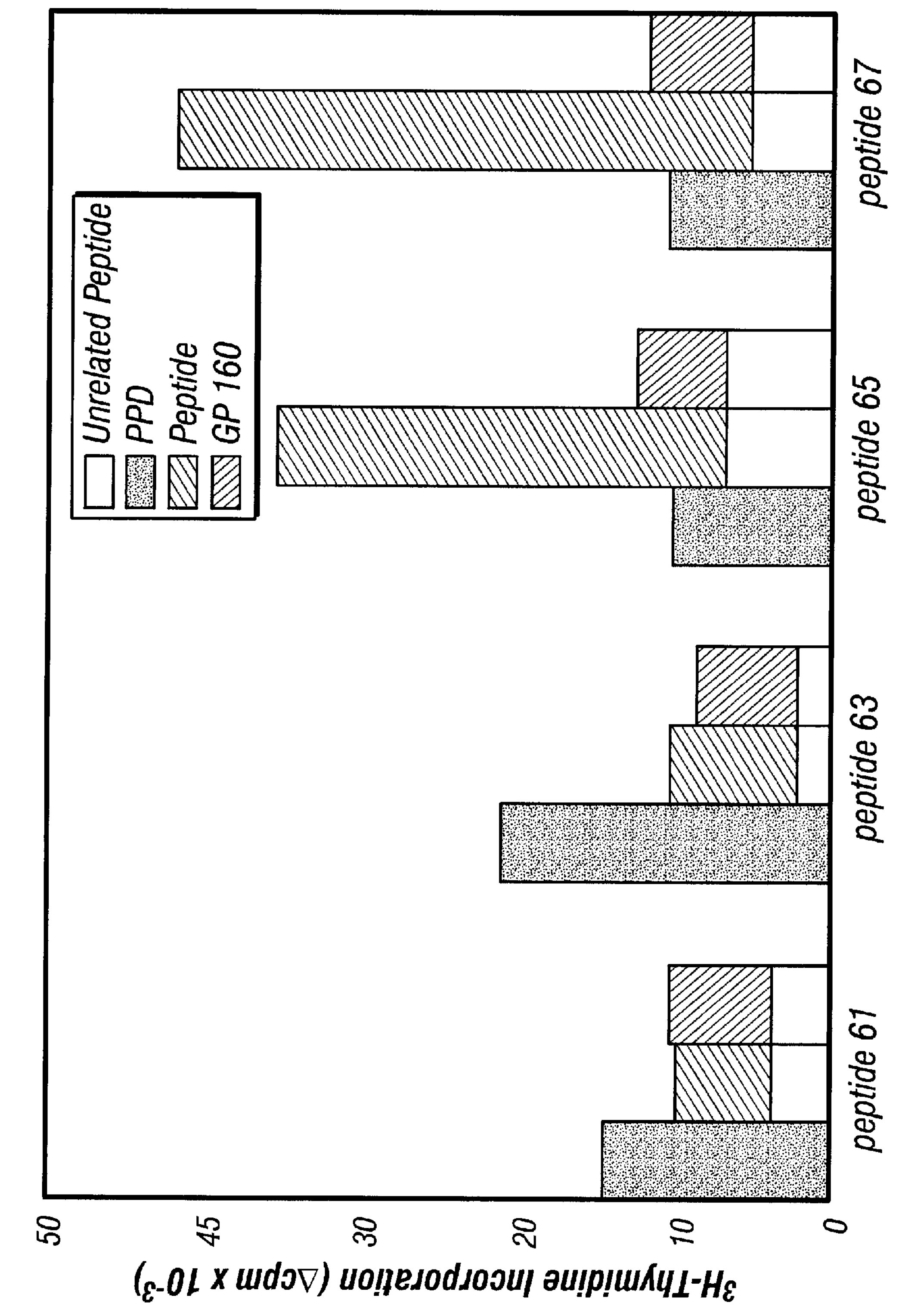
FIG. 3 is a graph similar to that of FIG. 2 except A.SWxBalb/c F1 mice were utilized as the animal hosts.
Figure 4:
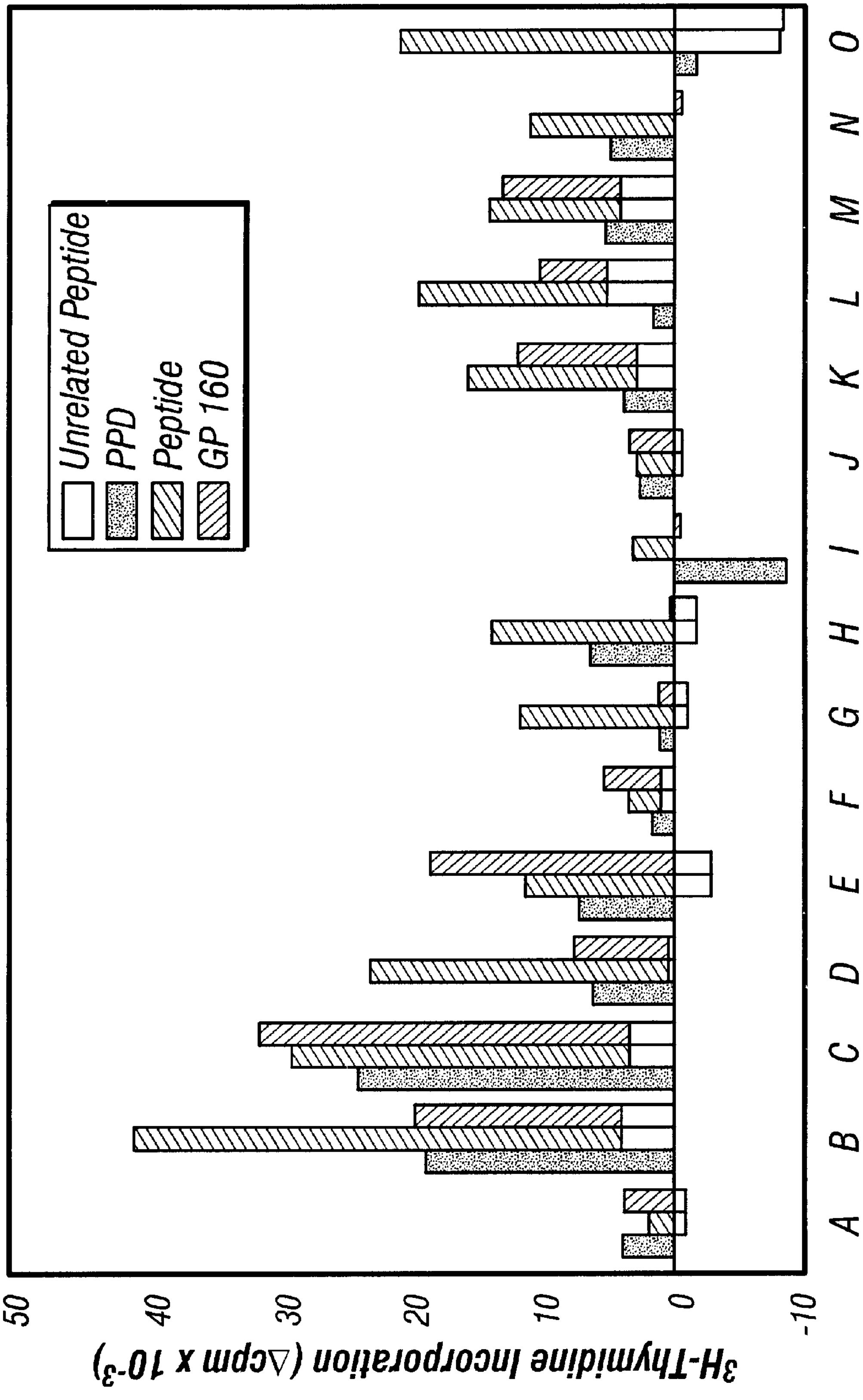
FIG. 4 is a graph similar to that of FIG. 2 in which multimers prepared from peptides 103 through 117 (a through o, respectively) were used to immunize B6C3 F1 mice.
Figure 5:
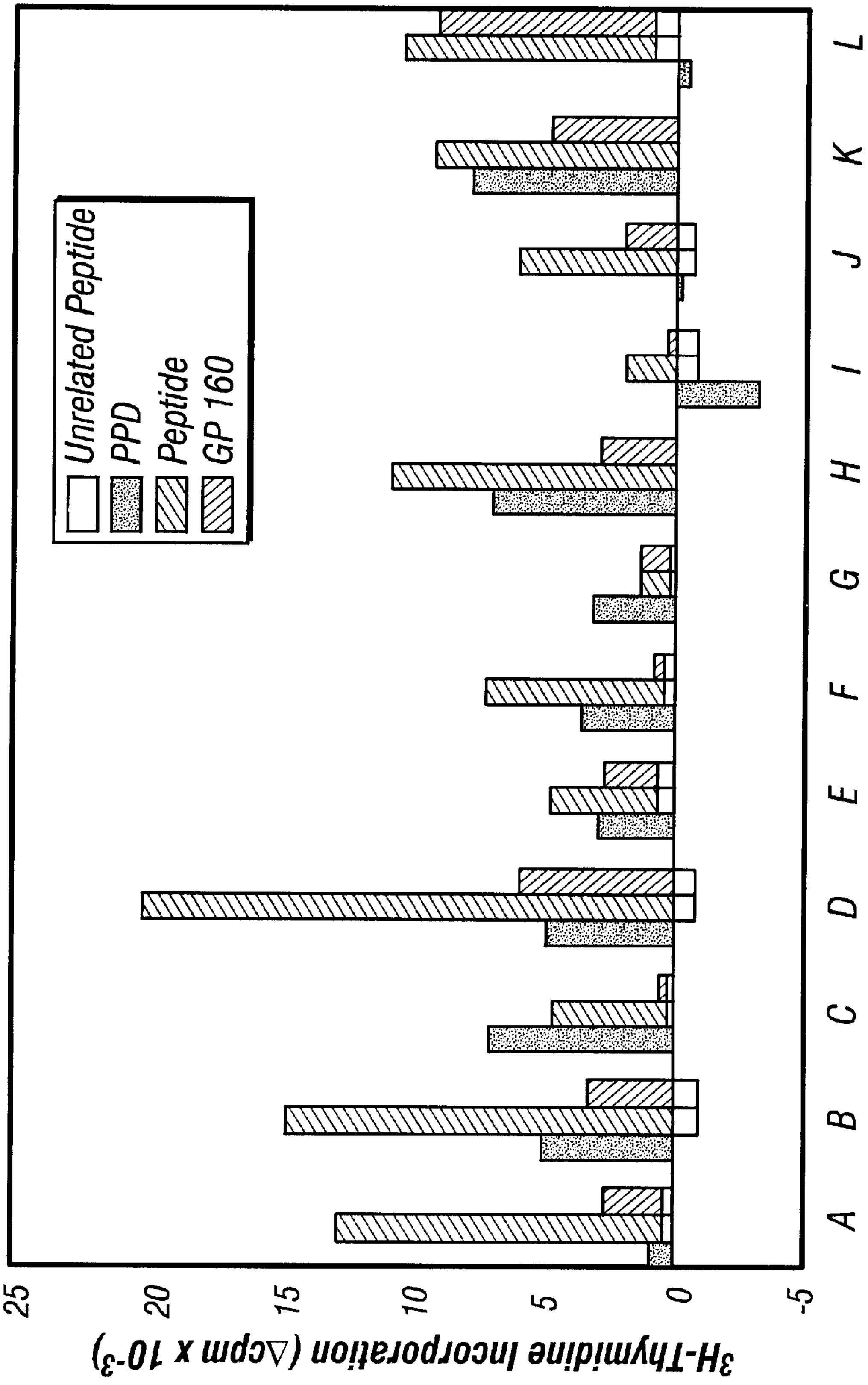
FIG. 5 is a graph similar to that of FIG. 4 except that A.SWxBalb/c mice were again used as the animal hosts.

The HIV agent is unique in that it infects cells involved in the immune response and can kill these cells. The host cell often involved is the T4 lymphocyte, a white blood cell that plays a central role in regulating the immune system. The virus binds to cell surface T4 protein which is implicated in the mediation of efficient T cell-target cell interactions. $T4^{+}$ lymphocytes interact with target cells expressing major histocompatibility (MHC) class II gene products.

Both T4 and MHC genes are members of the immunoglobulin gene family (Maddon et al., Cell, 47:333, 1986). The observation that T4 interacts with the exterior HIV envelope protein, gp120, prompted a structural comparison of the viral protein to immunoglobulin proteins. Interestingly, two regions of gp120 were found to share sequence homology with human immunoglobulin heavy chain constant regions (Maddon et al., Cell, 47:333, 1986).

Extrapolating from these observations, the present invention hinges to some extent upon the fact that gp120 has certain properties unique to human immunoglobulins. Furthermore, this similarity in structure may allow the virus to escape inactivation by antibody interaction. Still further, viral-antibody interaction may, in certain situations, increase the infectivity of the virus.

For example, recent work suggests that AIDS patients can and do have antibodies that neutralize the virus, as determined by in vitro laboratory tests. Yet these same patients die of the disease.

The present invention contemplates that antibodies binding to the virus may not interfere with and in some cases may even increase the virus' inherent ability to infect the patient's lymphoid cells. Recently, retrovirus infectivity was shown to be increased by binding of anti-retrovirus antibodies (Legrain et al., J. Virol., 60:1141, 1986). Therefore, an AIDS vaccine that primes the individual's immune system to make antibodies to viral surface proteins may enhance the infectivity of an already deadly virus. What is needed then is to stimulate only the individual's T cell immunity (for example, cytotoxic T cells or $CD8^{+}$ T cells) without involving an antibody response to viral proteins. Synthetic peptide immunogens can certainly achieve this result.

B. The Peptides

A peptide useful herein consists essentially of no more than about 30, and more preferably about 10 to about 25, amino acid residues and has a sequence that corresponds to a portion of a conserved domain of an HIV protein such as the gp120 envelope, gp41 envelope and core proteins. The gp41 and gp120 envelope proteins are portions of the precursor gp160 envelope protein.

It is therefore often convenient to refer to portions of the gp160 protein rather than the gp41 and gp120 molecules. Indeed, particularly preferred peptides have sequences that correspond to sequences of the first, second, third and fifth conserved domains of gp160, with the fifth domain being in the gp4l portion of the processed gp160 protein.

A useful peptide most preferably contains only those amino acid residues that are identical or homologous to (conservative substitutions for) residues present in a corresponding sequence of a conserved domain of an HIV protein. An additional number of residues of substantially any length can also be present at either or both termini of the peptide, up to a total of about 30 residence in a peptide. However, any additional residues must not interfere with the activity of the peptide, such as its ability to activate cytotoxic T cells and its substantial inability to induce production of antibodies that immunoreact with the corresponding native protein. Therefore, a peptide of this invention is said to "consist essentially" of an enumerated sequence.

The phrase "corresponds" as used herein means that an amino acid residue sequence has the same linear arrangement of the same amino acid residues as the sequence of the conserved HIV protein domain to which it "corresponds". However, it is well-known in the art that substitutions for amino acid residues can be made that are equivalent immunogenically.

In particular, conservative substitutions such as one hydrophobic or polar residue for another at one or more of many positions in a peptide frequently does not alter the immunogenic characteristics of the peptide. For example, an aspartic acid residue can be exchanged for a glutamic acid residue, or a leucine residue exchanged for an isoleucine. Thus, exchanges that destroy the amphipathic character of a peptide are excluded.

A first step in preparation of a peptide of the present invention is to prepare a number of peptides containing 7 to about 30, and preferably about 10 to about 25, amino acid residues in length and having an amino acid sequence that corresponds to a conserved domain of an HIV protein. For example, a large portion of gp41 is conserved among the seven strains of HIV-sequenced to date (Modrow et al., J. Virol., 61:570, 1987).

Computer programs have been developed that are useful in predicting T cell recognition sites and antibody binding sites within antigens (the latter known as B cell sites). Several computer programs can be used such as the be Lisi and Berzofsky program for T cell sites (Proc. Natl. Acad. Sci. USA, 82:7048, 1985), and for B cells - the Hopp and Woods program (J. Mol. Biol., 157:105, 1982) and the Sette et al., program (Mol. Immunol., 23:807, 1986. Short synthetic peptides were made from predicted T cell regions.

Using the computer program of Sette et al., (1986) to analyze the linear sequence of the HIV envelope proteins, several proposed T cell epitopes were selected from a first conserved segment of gp120 (Modrow et al., J. Virol., 61:570–578) as illustrative examples. Their sequences are as follows the amino-terminus at the left and carboxy-terminus on the right, in standard manner:

(1) CSAVEQLWVTVY;
(2) TTLFCASDAKAY;
(3) EVVLGNVTENFNM;
(4) QMHEDIISLWDQS; and
(5) QSLKPCVKLTPLC.

These peptides are predicted T cell epitopes within a 100 amino acid stretch of conserved sequences near the amino terminus of the gp120 protein. A recent report indicated that this region is active in stimulating T cell immunity (Ahearne et al., III International Conference on AIDS, held in Washington, D.C., Jun. 1–5, 1987, abstract # M.10.3, page 8).

Antigenic sites recognized by T cells have been reported to correlate with helical structures (either alpha helices or another type helix called a $3_{10}$ helical structure). Such antigenic sites are also thought to be protein segments displaying a polar/apolar character, forming a stable amphipathic structure with separated hydrophobic and hydrophilic surfaces and/or protein segments displaying a marked change in hydrophilicity between the first-half and the second-half of a block of amino acids (differential amphipathic structures).

In practice, using computer programs, the helical structures are identified by a consistent stretch of blocks of amino acids (each block being 6–7 residues in length) with angles (termed delta values) of 100°±20° (alpha helix) or 120°±15° ($3_{10}$ helical structure). Differential amphipathic structures are identified by peaks of differential hydrophilicity (See Table 1). For the purpose of selecting regions that are predicted to be poor antibody eliciting and/or binding sites, these structures should have negative mean hydrophilicity values. All of these values are listed below in Table 1 as the computer analysis of a conserved gp120 sequence (residues 35–137).

TABLE 1

ANALYSIS OF AN HIV-CONSERVED AMINO ACID SEQUENCE REGION SEQUENCE:
CSAVEQLWVTVYYCVPVWKEATTTLFCASDAKAYSTEVHNVWATHACVPTDPNPQEVVLCNVTENFNMWK
NNMVEQMHEDIIISLWDQSLKPCVKLTPLC

| BLOCK LENGTH 6 | BLOCK LENGTH 7 |
|---|---|
| HOPP/WOODS SCALE | KYTE/DOOLITTLE SCALE |
| MEAN HYDROPHILICITY = .0356494236 | MEAN HYDROPHILICITY = .0292929294 |
| MEAN DIFF. HYDR. = 4.72234043 | MEAN DIFF. HYDR. = 5.527957 |
| STANDARD DEV. = .41640836 | STANDARD DEV. = .436292101 |

| Block | | hydrophilicity | | amphipsthicity peaks | | Block | | hydrophilicity | | amphipathicity peaks | |
|---|---|---|---|---|---|---|---|---|---|---|---|
| No. | seq. | mean | diff. | angle | amph valve | No. | seq. | mean | diff. | angle | amph valve |
| 1 | CSAVEQ | .08 | 2.9 | 130 | 5.2603542 | 1 | CSAVEQL | −.65 | 6.7 | 110 | 13.7622165 |
| | | | | | | | | | | 180 | 4.05713223 |
| 2 | SAVEQL | −.05 | 3.1 | 106 | 6.07139973 | 2 | SAVEQLW | −.16 | 5.8 | 106 | 12.8605401 |
| 3 | AVEQLW | .46 | .8 | 118 | 8.61223123 | 3 | AVEQLWV | −.88 | 4.6 | 80 | 8.87890778 |
| | | | | | | | | | | 135 | 11.9637599 |
| 4 | VEQLWV | .3 | 1.6 | 134 | 9.74138842 | 4 | VEQLWVT | −.52 | 5.4 | 80 | 9.54449739 |
| | | | | | | | | | | 143 | 13.3879542 |
| 5 | EQLWVT | .49 | .1 | 123 | 8.21074778 | 5 | EQLWVTV | −.52 | 10.9 | 91 | 8.24956064 |
| | | | | | | | | | | 180 | 13.2857142 |
| 6 | QLWVTV | −.27 | 5.2 | 84 | 3.68722078 | 6 | QLWVTVY | −.83 | 2.8 | 108 | 6.12546694 |
| | | | | 180 | 7.99999744 | | | | | 180 | 19.4265565 |
| 7 | LWVTVY | −.69 | 4.3 | 80 | 3.40803117 | 7 | LWVTVYY | −1.15 | 5.5 | 88 | 5.78042364 |
| | | | | 145 | 6.79282004 | | | | | 180 | 12.6571412 |
| 8 | WVTVYY | −.77 | 7.6 | 117 | 5.2587283 | 8 | WVTVYYG | −.55 | 5.6 | 80 | 3.90743985 |
| | | | | 180 | 5.99999683 | | | | | 180 | 10.9428538 |
| 9 | VTVYYG | −1.61 | 2.8 | 80 | 2.27261392 | 9 | VTVYYGV | −1.28 | 5.2 | 80 | 5.68423569 |
| | | | | 180 | .999999507 | | | | | 112 | 7.47691013 |
| | | | | | | | | | | 180 | 12.428560L |
| 10 | TVYYGV | −1.61 | 1.2 | 80 | 2.36217496 | 10 | TVYYGVP | −.45 | 0 | 100 | 10.086216L |
| | | | | 180 | .999999844 | | | | | 180 | 11.5428464 |
| 11 | VYYGVP | −1.54 | 3 | 80 | 1.85508868 | 11 | VYYGVPV | −1.15 | 5.2 | 111 | 9.23573655 |
| | | | | 144 | 1.91242888 | | | | | 180 | 13.4571299 |
| 12 | YYGVPV | −1.54 | 3.2 | 80 | 1.8054094 | 12 | YYGVPVW | −.42 | 4.7 | 80 | 2.88605369 |
| | | | | 144 | 1.85463866 | | | | | 180 | 11.7142808 |
| 13 | YGVPVW | −.59 | 7.3 | 113 | 4.82991766 | 13 | YGVPVWK | −.05 | 3.1 | 80 | 4.28917765 |
| | | | | 180 | 7.09999547 | | | | | 132 | 11.3842845 |
| 14 | GVPVWK | .29 | 8 | 80 | 3.46214163 | 14 | GVPVWKE | .27 | 10.5 | 80 | 5.05560131 |
| | | | | 122 | 5.65042609 | | | | | 118 | 7.81868378 |
| | | | | | | | | | | 180 | 10.6285662 |
| 15 | VPVWKE | 1.06 | 12.4 | 80 | 4.21156022 | 15 | VPVWKEA | −.05 | 12.4 | 80 | 6.62653296 |
| | | | | 180 | 6.39999629 | | | | | 112 | 9.64156172 |
| | | | | | | | | | | 180 | 12.2571317 |
| 16 | PVWKEA | 1.23 | 3.6 | 80 | 7.35037792 | 16 | PVWKEAT | .65 | 4.1 | 87 | 11.1679208 |
| | | | | 180 | 5.39999818 | | | | | 180 | 8.14285043 |

TABLE 1-continued

ANALYSIS OF AN HIV-CONSERVED AMINO ACID SEQUENCE REGION SEQUENCE:
CSAVEQLWVTVYYCVPVWKEATTTLFCASDAKAYSTEVHNVWATHACVPTDPNPQEVVLCNVTENFNMWK
NNMVEQMHEDIISLWDQSLKPCVKLTPLC

BLOCK LENGTH 6
HOPP/WOODS SCALE
MEAN HYDROPHILICITY = .0356494236
MEAN DIFF. HYDR. = 4.72234043
STANDARD DEV. = .41640836

BLOCK LENGTH 7
KYTE/DOOLITTLE SCALE
MEAN HYDROPHILICITY = .0292929294
MEAN DIFF. HYDR. = 5.527957
STANDARD DEV. = .436292101

| Block | | hydrophilicity | | amphipsthicity peaks | | Block | | hydrophilicity | | amphipathicity peaks | |
|---|---|---|---|---|---|---|---|---|---|---|---|
| No. | seq. | mean | diff. | angle | amph valve | No. | seq. | mean | diff. | angle | amph valve |
| 17 | VWKEAT | 1.16 | 2.8 | 80 | 7.51038801 | 17 | VWKEATT | .52 | 1 | 83 | 11.107197 |
| | | | | 166 | 5.0399882 | | | | | 180 | 7.02856624 |
| 18 | WKEATT | 1.35 | 10.7 | 80 | 3.91623012 | 18 | WKEATTT | 1.22 | 6.2 | 108 | 6.03090101 |
| | | | | 120 | .300033045 | | | | | | |
| | | | | 180 | 3.89999705 | | | | | | |
| 19 | KEATTT | .71 | 6.7 | 80 | 3.87038548 | 19 | KEATTTL | .55 | B | 94 | 10.8301427 |
| | | | | 115 | 3.54324115 | | | | | 166 | 6.61371042 |
| 20 | EATTTL | –.09 | 4.7 | 108 | 4.84178659 | 20 | EATTTLF | –.4 | 8.3 | 95 | 8.81271666 |
| | | | | 180 | 4.89999533 | | | | | 180 | 7.39999914 |
| 21 | ATTTLF | –1 | 3.4 | 80 | 2.02960213 | 21 | ATTTLFC | –1.26 | 8.7 | 80 | 5.55101217 |
| | | | | 112 | 1.81597681 | | | | | 180 | 4.74285394 |
| | | | | 180 | .599999107 | | | | | | |
| 22 | TTTLFC | –1.09 | 4.1 | 80 | 2.54250479 | 22 | TTTLFCA | –1.26 | 9.2 | 80 | 4.52553122 |
| | | | | 136 | 1.39839332 | | | | | 180 | 3.65714207 |
| 23 | TTLFCA | –1.11 | 1.4 | 80 | 3.3632097 | 23 | TTLFCAS | –1.25 | 1.1 | 80 | 5.52825776 |
| | | | | 157 | .332518758 | | | | | 130 | 5.40023235 |
| 24 | TLFCAS | –.99 | 3.5 | 80 | 3.32553457 | 24 | TLFCASD | –.85 | 8.4 | 80 | 3.87846076 |
| | | | | 147 | 1.80392438 | | | | | 119 | 7.0806631 |
| | | | | | | | | | | 180 | 5.94284743 |
| 25 | LFCASD | –.42 | 8.1 | 80 | 2.06205252 | 25 | LFCASDA | –1.21 | 11.6 | 80 | 4.08829296 |
| | | | | 122 | 4.25830797 | | | | | 115 | 6.42577424 |
| | | | | 180 | 2.49999907 | | | | | 180 | 4.99999326 |
| 26 | PCASDA | –.21 | 6.8 | 80 | 3.58038047 | 26 | PCASDAK | –.11 | 12.7 | 94 | 5.27711073 |
| | | | | 139 | 4.84654054 | | | | | 150 | 9.17980169 |
| 27 | CASDAK | .71 | 6.7 | 113 | 3.91223995 | 27 | CASDAKA | .04 | 3.8 | 60 | 3.77241193 |
| | | | | 180 | 6.69999644 | | | | | 123 | 7.36122555 |
| | | | | | | | | | | 180 | 10.9428509 |
| 28 | ASDAKA | .6 | .6 | 80 | 2.28563281 | 28 | ASDAKAY | .58 | 9 | 80 | 3.54848783 |
| | | | | 157 | 6.39032513 | | | | | 150 | 10.4603253 |
| 29 | SDAKAY | .5 | 2.6 | 80 | 3.2211604 | 29 | SDAKAYS | 95 | 2.2 | 60 | .944789442 |
| | | | | 136 | 6.65130434 | | | | | 180 | 11.6571397 |
| 30 | DAKAYS | .5 | 8 | 60 | 3.01974627 | 30 | DAKAYST | .94 | 2.8 | 80 | .97233936 |
| | | | | 136 | 6.39531506 | 180 | 11.2571407 | | | | |
| 31 | AKAYST | –.07 | 4.4 | 115 | 5.43526965 | 31 | AKAYSTE | .94 | 4.7 | 80 | 4.07367275 |
| | | | | | | | | | | 148 | 10.3211839 |
| 32 | KAYSTE | .51 | 2.7 | 80 | 6.27726053 | 32 | KAYSTEV | .6 | 3.4 | 80 | 6.27920693 |
| | | | | 144 | 6.09214551 | | | | | 146 | 13.1855076 |
| 33 | AYSTEV | –.24 | 3.6 | 80 | 4.62499407 | 33 | AYSTEVH | –.03 | 1.49 | 80 | 5.29178076 |
| | | | | 180 | 6.99999752 | | | | | 139 | 9.29903238 |
| 34 | YSTEVH | .51 | 1.9 | 105 | 5.1518362 | 34 | YSTEVNH | .72 | 4 | 117 | 9.71864323 |
| | | | | 180 | 11.4999926 | | | | | | |
| 35 | STEVHH | .93 | .2 | 80 | .963303906 | 35 | STEVHNV | –.06 | 6.2 | 128 | 12.8286227 |
| | | | | 180 | 9.99999872 | | | | | | |
| 36 | TEVHNV | .63 | 1.6 | 60 | 3.30736594 | 36 | TEVHNVW | –.05 | .19 | 127 | 13.7231702 |
| | | | | 146 | 8.1502864 | | | | | | |
| 37 | EVHNVW | 1.26 | 3.4 | 134 | 10.0166439 | 37 | EVHNVWA | –.4 | 3.9 | 136 | 14.2693646 |
| 38 | VHNVWA | .68 | 1.3 | 131 | 9.91647749 | 38 | VHNVWAT | –.81 | 1 | 94 | 6.01966306 |
| | | | | | | | | | | 148 | 10.1310171 |
| 39 | HNVWAT | .86 | .19 | 116 | 6.66449943 | 39 | HNVWATH | –.28 | .4 | 88 | 4.30849285 |
| | | | | | | | | | | 180 | 11.8285674 |
| 40 | NVWAT0 | .86 | 1 | 123 | 6.65369771 | 40 | NVWATHA | –.46 | 1.8 | 84 | 5.69730511 |
| | | | | | | | | | | 161 | 10.5891462 |
| 41 | VWATHA | .75 | 1.69 | 133 | 9.64004539 | 41 | VWATHAC | –1.32 | .29 | 80 | 2.72499528 |
| | | | | | | | | | | 133 | 4.94525044 |
| | | | | | | | | | | 180 | 7.48570996 |
| 42 | WATHAC | .63 | 0 | 112 | 6.64659016 | 42 | WATHACV | –1.32 | 8.3 | 87 | 3.62934111 |
| | | | | | | | | | | 149 | 5.91098659 |
| 43 | ATHACV | .01 | 6.1 | 80 | 6.1106703 | 43 | ATHACVP | –1.22 | 3.5 | 80 | 6.638677 |
| | | | | 180 | 4.899999 | | | | | 146 | 6.75061693 |
| 44 | THACVP | .09 | 5.6 | 60 | 5.55283546 | 44 | THACVPT | –.86 | .29 | 80 | 6.79346425 |
| | | | | 180 | 5.39999651 | | | | | 135 | 5.22522487 |
| 45 | HACVPT | .1 | 4.4 | 60 | 5.17273346 | 45 | HACVPTD | –.46 | 10.6 | 80 | 5.70807306 |
| | | | | 180 | 5.39999715 | | | | | 180 | 7.8571393 |

TABLE 1-continued

ANALYSIS OF AN HIV-CONSERVED AMINO ACID SEQUENCE REGION SEQUENCE:
CSAVEQLWVTVYYCVPVWKEATTTLFCASDAKAYSTEVHNVWATHACVPTDPNPQEVVLCNVTENFNMWK
NNMVEQMHEDIIISLWDQSLKPCVKLTPLC

| BLOCK LENGTH 6 | BLOCK LENGTH 7 |
|---|---|
| HOPP/WOODS SCALE | KYTE/DOOLITTLE SCALE |
| MEAN HYDROPHILICITY = .0356494236 | MEAN HYDROPHILICITY = .0292929294 |
| MEAN DIFF. HYDR. = 4.72234043 | MEAN DIFF. HYDR. = 5.527957 |
| STANDARD DEV. = .41640836 | STANDARD DEV. = .436292101 |

| Block | | hydrophilicity | | amphipsthicity peaks | | Block | | hydrophilicity | | amphipathicity peaks | |
|---|---|---|---|---|---|---|---|---|---|---|---|
| No. | seq. | mean | diff. | angle | amph valve | No. | seq. | mean | diff. | angle | amph valve |
| 46 | ACVPTD | −.07 | 5.6 | 60 | 2.90366341 | 46 | ACVPTDP | −.16 | 14.3 | 80 | 3.93828552 |
| | | | | 160 | 4.39999676 | | | | | 180 | 6.14285612 |
| 47 | CVPTDP | .01 | 5.1 | 60 | 3.3008536 | 47 | CVPTDPN | .59 | 13.7 | 98 | 6.06728507 |
| | | | | 158 | 3.98100801 | | | | | 180 | 7.3999986 |
| 48 | VPTDPN | .21 | 5.1 | 80 | 3.65549613 | 46 | VPTDPNP | 1.18 | 6.6 | 102 | 5.52642539 |
| | | | | 180 | 5.09999822 | | | | | 180 | 10.0857082 |
| 49 | PTDPNP | .46 | 2.4 | 88 | 3.38300557 | 49 | PTDPNPQ | 2.28 | 2.8 | 93 | 2.49422442 |
| | | | | 180 | 3.59999964 | | | | | 180 | 5.91428331 |
| 50 | TDPNPQ | 5 | 2.2 | 80 | 2.71846268 | 50 | TDPNPQE | 2.55 | 2.8 | 91 | 2.95517847 |
| | | | | 170 | 3.80175964 | | | | | 180 | 5.65714194 |
| 51 | DPNPQE | 1.06 | 0 | 80 | 4.14976691 | 51 | DPNPQEV | 1.85 | 5.8 | 90 | 7.87338593 |
| | | | | 142 | 4.8530168 | 144 | 9.90699754 | | | | |
| 52 | PNPQEV | .31 | 1.5 | 143 | 4.58159443 | 52 | PNPQEVV | .75 | 11.6 | 104 | 9.82802 |
| | | | | | | | | | | 180 | 1.05713855 |
| 53 | NPQEVV | .06 | .4 | 100 | 4.89667866 | 53 | NPQEVVL | −.02 | 20.8 | 80 | 6.77921655 |
| | | | | | | | | | | 147 | 6.7977L978 |
| 54 | PQEVVL | −.27 | 8 | 80 | 4.88563707 | 54 | PQEVVLG | −.46 | 16.2 | 80 | 10.712972 |
| | | | | 180 | 4.59999854 | | | | | 180 | 6.25713895 |
| | | | | 80 | 4.22460786 | 55 | QEVVLGN | −.19 | 2.7 | 80 | 13.0618563 |
| 55 | QEVVLG | −.54 | 6.6 | 136 | 4.03179431 | | | | | 133 | 7.43431692 |
| 56 | EVVLGN | .54 | 3.2 | 80 | 4.7537475 | 56 | EVVLGNV | −1.29 | 4.6 | 80 | 14.8577324 |
| | | | | 143 | 5.23077801 | | | | | 148 | 12.1496517 |
| 57 | VVLGNV | −.29 | 1.9 | 80 | 1.81938005 | 57 | VVLGNVT | −1.69 | 12.2 | 80 | 7.97331492 |
| | | | | 132 | 1.94924385 | | | | | 146 | 9.18636992 |
| 58 | VLGNVT | 1.11 | 3.2 | 80 | 1.36359393 | 58 | VLGNVTE | −.59 | 7.6 | 98 | 14.3811965 |
| | | | | 180 | 2.59999936 | | | | | | |
| 59 | LGNVTE | −.36 | 4.3 | 115 | 6.05358251 | 59 | LGNVTEN | .51 | 7.6 | 99 | 13.327365 |
| | | | | 180 | 1.89999906 | | | | | | |
| 60 | GNVTEN | −.02 | 5.7 | 80 | 3.07264158 | 60 | CNVTENF | .65 | 4.5 | 96 | 12.4977417 |
| | | | | 130 | 5.08870785 | | | | | 180 | 11.4571327 |
| 61 | NVTENF | −.17 | 2.4 | 95 | 6.95264042 | 61 | NVTENFN | 1.1 | 4.2 | 104 | 13.410322 |
| | | | | 180 | .999997219 | | | | | 180 | 13.5999856 |
| 62 | VTENFN | −.17 | 3.2 | 94 | 6.87502696 | 62 | VTENFNM | .32 | 1.2 | 110 | 10.3891878 |
| | | | | 180 | .99999923 | | | | | 180 | 13.4285586 |
| 63 | TENFNM | −.14 | 6.4 | 80 | 4.31543897 | 63 | TENFNMW | 1.05 | 5.2 | 80 | 3.03805257 |
| | | | | 128 | 5.52726887 | | | | | 145 | 9.71945235 |
| 64 | ENFNMW | .5 | 1.6 | 80 | 6.56133261 | 64 | ENFNMWK | 1.51 | 1.3 | 80 | 2.85710325 |
| | | | | 146 | 7.0171153 | | | | | 134 | 11.1247084 |
| 65 | NFNMWK | .5 | 7.2 | 80 | 4.83053688 | 65 | NFNMWKN | 1.51 | 4.1 | 80 | 3.36279834 |
| | | | | 147 | 5.17803036 | | | | | 180 | 10.6857106 |
| 66 | FNMWKN | .5 | 10.2 | 80 | 5.34455775 | 66 | FNMWKNN | 1.51 | 12.1 | 148 | 9.50267953 |
| | | | | 147 | 5.54090488 | | | | | | |
| 67 | NMWKNN | .94 | 1.09 | 84 | 6.47598203 | 67 | NMWKNNM | 1.64 | 2.6 | 80 | 10.3115109 |
| | | | | | | | | | | 147 | 8.85827898 |
| 68 | MWKNNM | .7 | 6 | 80 | 6.10042863 | 68 | MWKNNMV | .54 | 5.5 | 80 | 9.63372205 |
| | | | | 140 | 5.32945602 | | | | | 127 | 7.14594883 |
| | | | | | | | | | | 180 | 1.74284865 |
| 69 | WKNNMV | .66 | 9.2 | 80 | 2.50153618 | 69 | WKNNMVE | 1.31 | 10.9 | 80 | 11.0435161 |
| | | | | 120 | 4.27897212 | | | | | 141 | 7.54448264 |
| | | | | 180 | .599996358 | | | | | | |
| 70 | KNNMVE | .6 | 3.2 | 80 | 5.58419524 | 70 | KNNMVEQ | 1.68 | 8.1 | 80 | 12.1178417 |
| | | | | 142 | 6.14937436 | | | | | | |
| 71 | NNMVEQ | .13 | 2.6 | 96 | 4.73472565 | 71 | NNMVEQM | .95 | 0 | 90 | 14.9537026 |
| 72 | NMVEQM | −.12 | 4.5 | 100 | 6.00683252 | 72 | NMVEQMH | .28 | 3.7 | 96 | 14.1948524 |
| | | | | | | | | | | 180 | 2.31426043 |
| 73 | MVEQMH | .51 | 2.7 | 115 | 9.19182903 | 73 | MVEQMHE | .28 | 3.7 | 97 | 14.1805622 |
| | | | | | | | | | | 180 | 4.1142807 |
| 74 | VEQMHE | 1.23 | 4 | 116 | 8.62558323 | 74 | VEQMHED | 1.05 | 3.7 | 94 | 14.283656 |
| | | | | | | | | | | 149 | 5.84410789 |
| 75 | EQMHED | 1.98 | 8.1 | 80 | 6.34436198 | 75 | EQMHEDI | 1.39 | .1 | 91 | 12.326519 |
| | | | | | | | | | | 180 | 4.59999931 |
| 76 | QMHEDI | .31 | 3.9 | 80 | 12.6132845 | 76 | QMHEDII | .64 | 1.2 | 90 | 12.1656749 |
| | | | | 180 | 12.4999944 | | | | | 166 | 4.38843143 |

TABLE 1-continued

ANALYSIS OF AN HIV-CONSERVED AMINO ACID SEQUENCE REGION SEQUENCE:
CSAVEQLWVTVYYCVPVWKEATTTLFCASDAKAYSTEVHNVWATHACVPTDPNPQEVVLCNVTENFNMWK
NNMVEQMHEDIISLWDQSLKPCVKLTPLC

| BLOCK LENGTH 6 | BLOCK LENGTH 7 |
|---|---|
| HOPP/WOODS SCALE | KYTE/DOOLITTLE SCALE |
| MEAN HYDROPHILICITY = .0356494236 | MEAN HYDROPHILICITY = .0292929294 |
| MEAN DIFF. HYDR. = 4.72234043 | MEAN DIFF. HYDR. = 5.527957 |
| STANDARD DEV. = .41640836 | STANDARD DEV. = .436292101 |

| Block | | hydrophilicity | | amphipsthicity peaks | | Block | | hydrophilicity | | amphipathicity peaks | |
|---|---|---|---|---|---|---|---|---|---|---|---|
| No. | seq. | mean | diff. | angle | amph valve | No. | seq. | mean | diff. | angle | amph valve |
| 77 | MHEDII | −.89 | 16.7 | 80 | 14.797617 | 77 | MHEDIIS | .25 | 3.9 | 80 | 10.5667494 |
| | | | | 147 | 7.21621384 | | | | | 157 | 1.58692131 |
| 78 | HEDIIS | −.62 | 23.7 | 80 | 15.0471601 | 78 | HEDIISL | −.02 | 11.3 | 114 | 9.62047164 |
| | | | | 141 | 7.85709809 | | | | | 180 | 5.08570813 |
| 79 | EDIISL | −1.59 | 7.5 | 81 | 15.6576936 | 79 | EDIISLW | .18 | 7.3 | 116 | 9.13994576 |
| | | | | 100 | 2.09999726 | | | | | 180 | 5.31426206 |
| 80 | DIISLW | −1.52 | 12.9 | 80 | 12.6258975 | 80 | DIISLWD | .18 | .69 | 80 | 2.75431712 |
| | | | | 140 | 13.6672029 | | | | | 123 | 11.6897921 |
| | | | | | | | | | | 180 | 1.31428269 |
| 81 | IISLWD | −1.52 | 18.3 | 80 | 4.8601113 | 81 | IISLWDV | .18 | 10.7 | 100 | 7.92396483 |
| | | | | 124 | 10.62247 | | | | | 180 | 5.31428532 |
| 82 | ISLWDQ | −.32 | 15.1 | 80 | 6.41076427 | 82 | ISLWDQS | 55 | 12.6 | 80 | 6.14412544 |
| | | | | 164 | 9.73681878 | | | | | 180 | 7.05713941 |
| 83 | SLWDQS | .9 | 1.6 | 87 | 6.61515331 | 83 | SLWDQSL | .27 | 2.6 | 80 | 12.1215222 |
| | | | | | | | | | | 147 | 7.59794494 |
| 84 | LWDQSL | .55 | 5.9 | 80 | 6.51625779 | 84 | LWDQSLK | .71 | .3 | 81 | 13.5587838 |
| | | | | 141 | 6.2593098 | | | | | 149 | 10.5987673 |
| 85 | WDQSLK | 1.35 | 5.1 | 80 | 5.92760332 | 85 | WDQSLKP | 1.46 | 6.2 | 89 | 9.49759941 |
| | | | | 151 | 5.29558905 | | | | | 180 | 7.48S71071 |
| 86 | DVSLKP | .76 | 2.3 | 87 | 5.08496961 | 86 | DQSLKPC | 1 | 4.8 | 97 | 12.4768136 |
| | | | | 180 | 7.89999554 | | | | | | |
| 87 | QSLKPC | .11 | 3.3 | 122 | 5.20035816 | 87 | QSLKPCV | −.1 | 5.6 | 95 | 14.484075 |
| | | | | 159 | 5.67278754 | | | | | | |
| 88 | SLKPCV | −.17 | 4 | 89 | 4.72437198 | 88 | SLKPCVK | −.05 | 3.7 | 100 | 14.2863777 |
| | | | | 180 | 5.59999792 | | | | | 180 | 12.542844 |
| 89 | LKPCVK | .28 | .7 | 97 | 7.84178318 | 89 | LKPCVKL | −.7 | 5.8 | 107 | 14.9608929 |
| | | | | 180 | 8.29999305 | | | | | 180 | 14.799984 |
| 90 | KPCVKL | .28 | 2.3 | 99 | 7.08316366 | 90 | KPCVKLT | −.06 | 2.2 | 107 | 11.1829906 |
| | | | | 180 | 8.29999385 | | | | | 180 | 12.4571346 |
| 91 | PCVKLT | −.29 | 3.3 | 132 | 5.51747666 | 91 | PCVKLTP | .39 | 3.6 | 127 | 12.9245369 |
| 92 | CVKLTP | −.29 | 2.7 | 129 | 5.47302639 | 92 | CVKLTPL | −1.16 | 1.3 | 80 | .824544342 |
| | | | | | | | | | | 133 | 13.7445971 |
| 93 | VKLTPL | −.42 | 1.9 | 80 | 1.72145914 | 93 | VKLTPLC | −1.16 | .6 | 80 | 2.17205276 |
| | | | | 138 | 6.86166129 | | | | | 132 | 12.8299583 |
| 94 | KLTPLC | .34 | 3.6 | 124 | 5.85689593 | | | | | | |

Five peptides were selected from within residues 35 through 137 of the gp120 surface protein of HIV.

Peptide number (1, above) which spans blocks 1–5 (6 amino acids per block) has delta values (termed ANGLE) consistent with a helical structure as predicted by both the Hopp/Woods computer program (block length of 6 amino acids) and the Kyte/Doolittle computer program (block length of 7 amino acids).

Peptide number (2, above) which spans blocks 23–28 has a peak of differential hydrophilicity (a marked change in mean hydrophilicity between the first-half and second-half of a block of amino acids) that is predicted by both programs.

Peptide number (3, above) which spans blocks 56–63 has delta values consistent with a helical structure (Kyte/Doolittle) and a peak of hydrophilicity (both programs).

Peptide number (4, above) which spans blocks 76–83 has a peak of differential hydrophilicity (both programs).

Peptide number (5, above) which spans blocks 87–94 has delta values consistent with helical structures (both programs).

All five of these peptides exhibit negative mean hydrophilicity values indicating that they are poor antibody binding sites.

Five other conserved regions of the two HIV envelope proteins can be similarly analyzed and putative T cell-active peptides selected. These regions include residues 204–279 (C2 or conserved region 2), 415–458 (C3), 470–510 (C4), 511–616 (C5) and 654–745 (C6) (Modrow et al., J. Virology, 61:570,1987).

Similar computer analysis of the gag gene of HIV has revealed several T cell epitopes from within the core or gag gene of HIV (Coates et al., Nature, 326:549, 1987). These peptides are shown below, with their residue position numbers in the protein shown above each peptide.

```
56       62
  EGCRQIL

74       85
  ELRSLYNTVAT

170           180
  VIPMFSALSEG
```

-continued

```
199        206
   AMQMLKET

298        305
   YVDREYKT

333        342
   KTILKALGPA

346        355
   EMMTACQGV

367        375
   AEAMSQVTN
```

Such synthetic peptides (either from the surface proteins or the core proteins) are able to induce a cell-mediated response sufficient to destroy virus-infected cells bearing the corresponding HIV protein epitopes on their cell surfaces, or as suggested by the work Walker et al., (Science, 234:1563–1566, 1986) inhibit the growth of the virus.

As an alternate approach to identify T cell active peptides, it may be necessary to thoroughly cover the protein sequence in question. In this case, overlapping 15-amino acid peptides (15 mers) can be made (the second peptide overlaps with the C-terminal 5 amino acids of the first peptide, the third overlaps the second, etc.) across the complete conserved amino acid sequence of both gp120 and gp41.

All of these peptides can be made, for example, by the solid phase Merrifield-type synthesis but can also be made by liquid phase synthesis or recombinant DNA-related methods known to those skilled in the relevant arts. A further description of the basic solid phase synthesis method, for example, can be found in the literature (i.e., M. Bodansky et al., Peptide Synthesis, John Wiley and Sons, Second Edition, 1976, as well as in other reference works known to those skilled in this type of chemistry. The so-called "bag" technique described in Houghten, Proc. Natl. Acad. Sci. USA, 82:5131–5135 (1985) is also useful. Appropriate protective groups usable in such synthesis and their abbreviations will be found in the above reference, as well as in J. F. W. Mcomie, Protective Groups in organic Chemistry, Plenum Press, New York, 1973).

Several peptides were prepared using the before-described techniques. Illustrative peptides so prepared are discussed hereinafter.

Of those peptides that can be so prepared, an exemplary peptide useful for preparing a multimer as discussed hereinafter includes an amino acid residue sequence whose formula corresponds to one of those shown below, from left to right and in the direction from amino-terminus to carboxy-terminus:

—EQLWVTVYYGVPV—,
—VYYGVPVWKEA—,
—GVPVWKEATTLFC—,
—AHKVWATHACV—,
—CVPTNPVPQEVV—,
—VLENVTENFNM—,
—NNMVEQMHEDII—,
—EQMHEDIISLWDQ—,
—LWDQSLKPCVKLT—,
—SLKPCVKLTPLC—,
—SVITQACSKVSFE—,
—FEPIPIHYCAFPGF—,
—KKFNGTGPCTN—,
—GTGPCTNVSTVQC—,
—VQCTHGIRPVVSTQ—,
—YLRDQQLLGIWGC—,
—FLGFLGAAGSTMGAASLTLTVQARQ—,
—CRIKQIINMWQGVGKAMYA—,
—CRIKQIINMWQGVGKAMYAPPIGGQIRC—,
—EGCRQIL—,
—ELRSLYNTVAT—,
—VIPMFSALSEG—,
—AMQMLKET—,
—YVDREYKT—,
—KTILKALGPA—, and
—EMMTACQGV—.

In the list above, and elsewhere herein, hyphens at the amino- and carboxy-termini of a sequence are intended to imply that one or more additional amino acid residues can be present in a peptide sequence, as discussed before.

Preferably, a useful peptide having a sequence shown hereinabove is utilized without additional residues at either terminus, except for cysteine and lysine residues as are discussed hereinafter. Such a peptide has a sequence, as discussed before, that corresponds to a formula shown below:

EQLWVTVYYGVPV,
VYYGVPVWKEA,
GVPVWKEATTLFC,
AHKVWATHACV,
CVPTNPVPQEVV,
VLENVTENFNM,
NNMVEQMHEDII,
EQMHEDIISLWDQ,
LWDQSLKPCVKLT,
SLKPCVKLTPLC,
SVITQACSKVSFE,
FEPIPIHYCAFPGF,
KKFNGTGPCTN,
GTGPCTNVSTVQC,
VQCTHGIRPVVSTQ,
YLRDQQLLGIWGC,
FLGFLGAAGSTMGAASLTLTVQARQ,
CRIKQIINMWQGVGKAMYA,
CRIKQIINMWQGVGKAMYAPPIGGQIRC,
EGCRQIL,
ELRSLYNTVAT,
VIPMFSALSEG,
AMQMLKET,
YVDREYKT,
KTILKALGPA, and
EMMTACQGV.

A preferred peptide includes a sequence, as discussed before, that corresponds to a formula shown below.

—LWDQSLKPCVKLT—,
—GVPVWKEATTLFC—,
—GTGPCTNVSTVQC—,
—YLRDQQLLGIWQC—,
—FLGFLGAAGSTMGAASLTLTQARQ—,
—CRIKQIINMWQGVGKAMYA—,
—EQLWVTVYYGVPV—,

—VYYGVPVWKEA—, and

—SVITQACSKVSFE—.

A particularly preferred peptide, except for the lysine and cysteine residues discussed hereinafter, corresponds to a formula shown below.

LWDQSLKPCVKLT,

GVPVWKEATTLFC,

GTGPCTNVSTVQC,

YLRDQQLLGIWQC,

FLGFLGAAGSTMGAASLTLTQARQ,

CRIKQIINMWQGVGKAMYAPPIGGQIRC,

EQLWVTVYYGVPV,

VYYGVPVWKEA, and

SVITQACSKVSFE.

Some of the before-enumerated peptides have been disclosed in whole or in part by others as containing T cell epitopes. However, those disclosures did not teach or suggest the multimers that are discussed hereinafter.

For example, Berzofsky et al., Nature, 334:706–708 (1988) and Cease et al., Proc. Natl. Acad. Sci. USA, 84:4249–4253 (1987) disclosed two peptides having the sequences, as shown before, that are represented by the formulas KQIINMWQGVGKAMYA, and

HEDIISLWDQSLK that were said to stimulate T cells of mice immunized with the peptide or a recombinant molecule containing a large portion of the gp120 molecules as well as in humans who had previously been immunized with a recombinant vaccinia virus that expressed the HIV gp160 protein.

Takahashi et al., Proc. Natl. Acad. Sci. USA, 85:3105–3109 (1988) prepared fifty-five peptides corresponding to much of the gp160 molecule of HIV, and studied the T cell stimulatory effect of those peptides on cells from mice immunized with a recombinant vaccinia virus that expressed gp160. Those workers found a single peptide from the gp120 sequence to be an immunodominant site for stimulation of cytotoxic T lymphocytes, and that that peptide overlapped a B cell epitope capable of evoking virus-neutralizing antibody responses in both animals and humans. That epitope was located at positions 308–322 of gp120 and was said by those workers to be a highly variable sequence among different isolates of HIV.

Thus, being a B cell epitope and being highly variable in sequence, the immunodominant peptide of Takahashi et al. has little bearing here. Four additional peptides (positions 343–357, 637–651, 657–671 and 780–794) were also said to appear to marginally sensitize target cells.

Of the preferred and particularly preferred peptides disclosed hereinbefore that are useful for preparation of the multimers discussed hereinafter, several are believed to be new, whereas others have been disclosed in whole or in part of others. Those new peptides are most preferred and consist essentially of a sequence, written from left to right and in the direction from amino-terminus to carboxy-terminus, represented by a formula shown below:

YLRDQQLLGIWGC,

FLGFLGAAGSTMGAASLTLTQARQ,

EQLWVTVYYGVPV,

VYYGVPVWKEA,

SVITQACSKVSFE,

GVPVWKEATTLFC,

AHKVWATHACV,

CVPTNPVPQEVV,

SLKPCVKLTPLC,

FEPIPIHYCAFPGF,

EGCRQIL,

ELRSLYNTVAT,

VIPMFSALSEG,

AMQMLKET,

YVDREYKT,

KTILKALGPA, and

EMMTACQGV.

The above new peptides can also be included in a longer peptide having a sequence of up to about 30 amino acid residues. Such a longer peptide consists essentially of an amino acid residue sequence, from left to right and in the direction from amino-terminus to carboxy-terminus, represented by a formula shown below:

—YLRDQQLLGIWGC—,

—FLGFLGAAGSTMGAASLTLTQARQ—,

—EQLWVTVYYGVPV—,

—VYYGVPVWKEA—,

—SVITQACSKVSFE—,

—GVPVWKEATTLFC—,

—AHKVWATHACV—,

—CVPTNPVPQEVV—,

—SLKPCVKLTPLC—,

—FEPIPIHYCAFPGF—,

—EGCRQIL—,

—ELRSLYNTVAT—,

—VIPMFSALSEG—,

—AMQMLKT—,

—YVDREYKT—,

—KTILKALGPA—, and

—EMMTACQGV—.

The most preferred peptides of the group described immediately above consist essentially of a sequence of up to about 30 amino acid residues, as shown before, represented by a formula shown below:

—YLRDQQLLGIWGC—,

—FLGAAGSTMGAASLTLTVARQ—,

—EQLWVTVYYGVPV—,

—VYYGVPVWKEA—,

—SVITQACSKVSFE—, and

—GVPVWKEATTLFC—,

C. The Multimer and Composition

A useful peptide is itself utilized in an aqueous composition or inoculum that contains dissolved or dispersed therein a multimeric form of the peptide. The peptide multimer is usually hereinafter referred to as being dispersed in water for greater ease of expression and since a solution can be viewed as the ultimate form of a dispersion.

These peptides elicit a T cell response but not a substantial antibody response, when introduced into an immunocompetent host animal, (a mammal) such as a laboratory mouse or rat, a goat, an ape such as chimpanzee or a human. Therefore, when suitably prepared, a peptide multimer composition of the present invention stimulates T cell immunity (e.g., cytotoxic T cells) without producing a substantial humoral antibody response. The peptide multimer composition of the present invention primes T cells in a way that, when the infecting virus appears at a later date, memory T cells are activated to result in a cell-mediated immune response that destroys target cells that have the corresponding HIV protein or a portion thereof on their cell surfaces, and thereby the virus.

The activation of only T cells without an antibody response is important because it is believed that antibodies to most regions of the viral envelope protein may stimulate the infectivity of the virus. This latter point renders most viral surface envelope antigen preparations (e.g., intact gp120 and gp41 that contain both B- and T-cell epitopes) ineffective as vaccines. Barnes, Science, 236:255, (1987). The Barnes article reported that about 20 chimpanzees had been given various prototype vaccines (containing B- and T-cell epitopes) and some were challenged by injecting virus, but the results indicated that none of the vaccines prevented infection by infectious HIV. In contrast, this invention provides a suitable T cell response that produces cytotoxic T cells or other types of T cell responses that kill or otherwise neutralize target cells such as T lymphocytes that express an HIV protein or a portion of an HIV protein on the target cell surface.

It should be emphasized that an effective peptide multimer can in some cases induce a low to moderate level antibody response and still be useful in an effective composition. In this case, the induced anti-peptide antibodies are incapable of recognizing or detecting the mature native protein such as gp160 to which the peptide of the multimer corresponds in sequence. Thus, the anti-peptide antibodies induced by the T cell active peptide must not be substantially capable of binding to the intact, infectious virus. It is well known that anti-peptide antibodies to certain regions of a given protein may not recognize the native protein (for example, see the work of Ho et al., J. Virol., 61:2024, 1987).

The use of synthetic peptides that are T cell active but that are not immunogenic for native virus (anti-peptide antibodies that are unable to detect or immunoreact with the virus particle) can have an added advantage in that inherent immunological memory should be superior for peptide vaccines of the present invention.

The composition or inoculum contains a before-described peptide in a multimeric form. Exemplary of such multimers are surfactant-like micelles and polymers, examples of each of which are discussed hereinafter.

In one type of multimer synthesis, the N-terminal end of each peptide is linked to a di-$C_{12}$–$C_{18}$ fatty acid amide of a lysine-terminated peptide spacer such as a dipalmityl-lysyl-glycyl-glycyl sequence to serve as a carrier as described by T. P. Hopp (Mol. Immunol., 21:13, 1984). Other useful $C_{12}$–$C_{18}$ fatty acids include lauric, myristic, stearic, oleic and palmitoleic acids.

An example of this type of structure is shown below:

α = alpha amino group of lysine

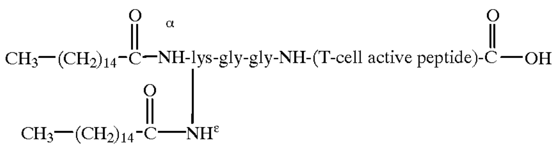

ε = epsilon amino group of lysine

In addition to the amino-terminal lysyl residue, the spacer peptide can contain one to about five additional residues. Substantially any amino acid residue can be utilized so long as it does not interfere with the T cell immunizing capacity of an aqueous composition containing the multimer or with the capacity of the di-amide reaction product to form surfacetant-like micelles in an aqueous composition. One to about three glycyl residues per spacer peptide are preferred.

The before-described peptide and the amino-terminal lysyl residue-containing peptide spacer are peptide-bonded together, and can thus be viewed as a composite polypeptide. The useful diamide is thus a reaction product of the alpha- and epsilon-amino groups of the amino-terminal lysyl residue and two moles per composite polypeptide of the $C_{12}$–$C_{18}$ fatty acid. The composite polypeptide can thus be prepared as a single sequence and amidified before or after removal from the resin, where solid phase synthesis is used, by conventional techniques.

The phrase "surfactant-like micelle" is used herein to emphasize that, in an aqueous composition, the di-amidolysyl composite polypeptide appears to form micelles similar to those formed by surfactants and to distinguish such multimers from submicroscopic structural units of protoplasm built up from polymeric molecules that are also sometimes referred to as micelles. The word "micelle" is also sometimes used herein, and when so used has the same meaning as surfactant-like micelle.

Another multimer form of a previously described peptide is a polymer having a plurality of peptide repeating units. In this case, a peptide containing two terminal cysteines as part of its natural sequence can be selected and synthesized. A peptide lacking such cysteines can be modified by the addition of one or two extra cysteines to the N- and C-terminal ends, respectively. The presence of two cysteines per peptide permits polymerization of the subunit peptide by air oxidation to form oxidized cysteine(cystine)-linked polymers and/or cyclic peptides. Such multimers enhance immune recognition of the peptide without the need of a carrier.

An example of this type of structure is shown below:

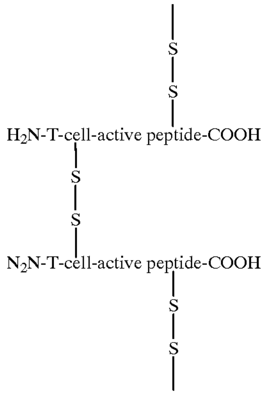

The lysine-terminated spacer peptide can contain one to about five amino acid residues in addition to the lysyl residue, and the one or two added terminal cysteine residues are not included in counting the length of a peptide of the present invention. A peptide containing terminal cysteine residues is referred to as a di-cysteine-terminated peptide or more simply, a di-Cys peptide. Details for preparing polymers containing di-Cys peptide repeating units are provided hereinafter.

It should also be noted that a peptide multimer of a composition can contain more than one, active, T cell stimulating peptide as described previously. The inclusion of more than one such active peptide permits activation by more than a single T cell epitope to a single HIV protein, as well as to a plurality of HIV proteins. Such inclusion of peptides of different sequences can also avoid non-response in the host animal that is immunized. In addition, a multimer can also include an inactive peptide; i.e., a peptide that does not induce T cell activation or antibodies that immunoreact with a native HIV protein, to enhance water dispersibility, for example.

An aqueous composition (inoculum) of the present invention comprises an immunologically effective amount of a before-described peptide multimer dissolved or dispersed in a pharmaceutically acceptable aqueous medium. Such compositions are also referred to as inocula, as noted before.

The phrase "pharmaceutically acceptable" refers to molecular entities and compositions that do not produce an allergic or similar untoward reaction when administered to a human.

The preparation of an aqueous composition that contains an immunizing molecule such as a before-described peptide multimer as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The active immunogenic peptide multimer is dissolved or dispersed in an excipient that is pharmaceutically acceptable and compatible with the active T cell immunogen as is well known. Suitable excipients are, for example, water, saline, phosphate buffered saline (PBS), dextrose, glycerol, ethanol, or the like and combinations thereof. In addition, if desired, the composition can contain minor amounts of auxiliary substances such as wetting or emulsifying agents, pH buffering agents or adjuvants that enhance the effectiveness of the vaccine.

The composition is conventionally administered (introduced) parenterally, by injection, for example, intraperitoneally, intravenously, intradermally, subcutaneously or intramuscularly. Additional formulations that are suitable for other modes of administration include suppositories and, in some cases, oral formulations. For suppositories, traditional binders and carriers can include, for example, polyalkalene glycols or triglycerides; such suppositories can be formed from mixtures containing the active ingredient in the range of 0.5 percent to 10 percent, preferably 1–2 percent. Oral formulations include such normally employed excipients as, for example, pharmaceutical grades of mannitol, lactose, starch, magnesium stearate, sodium saccharine, cellulose, magnesium carbonate and the like.

A peptide multimer can be formulated into a composition in a neutral or salt form. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Similarly, peptides and peptide multimers of this invention can form salts with fluosilicic acid. These salts are useful as mothproofing agents in accordance with the teachings of U.S. Pat. No. 1,915,334 and U.S. Pat. No. 2,075,359. The instant peptides and peptide multimers also form salts with thiocyanic acid which, in turn, can be condensed with formaldehyde to form resinous materials useful as pickling inhibitors in accordance with U.S. Pat. No. 2,425,320 and U.S. Pat. No. 2,606,155. Salts of the peptide and peptide multimers with trichloroacetic acid are useful as herbicides against Johnson grass, yellow foxtail, Bermuda grass, quack grass, and the like. Salts formed between ammonia and a carboxylic acid present in the peptides and peptide multimers of this invention can be used as a source of nitrogen for leguminous plants such as peas.

A composition is administered in a manner compatible with the dosage formulation, and in such amount as is immunologically effective. By "immunologically effective amount" is meant an amount of composition is used that contains an amount of a peptide multimer sufficient to induce cellular immunity in the host animal (mammal) such as by the induction of anti-HIV cytotoxic T cells. The presence of such cytotoxic T cells is assayed as discussed hereinafter.

The quantity of multimer peptide and volume of composition to be administered depends on the host animal to be immunized, the capacity of the host animal's immune system to activate T cells, and the degree of protection desired. Precise amounts of active peptide multimer required to be administered depend on the judgment of the practitioner and are peculiar to each individual. However, suitable dosage ranges are of the order of about 10 micrograms ($\mu$g) to about 500 milligrams, preferably about 50 $\mu$g to about 1 mg, and more preferably about 100 micrograms of active ingredient peptide multimer per individual. A minimal volume of a composition required to disperse the immunizing amount of peptide multimer is typically utilized. Suitable regimes for initial administration and booster shots are also variable, but are typified by an initial administration followed in one or two week intervals by a subsequent injection or other administration.

A composition can also include an adjuvant as part of the excipient. Adjuvants such as complete Freund's adjuvant (CFA), incomplete Freund's adjuvant (IFA) for use in laboratory host mammals are well known in the art, and are used illustratively herein. Pharmaceutically acceptable adjuvants such as alum can also be used.

Typical mammals (host animals) used in practicing a method of this invention include mice, rabbits, goats, primates, humans and the like.

In a usual screening procedure, each peptide multimer preparation is first assayed in mice, for example, to screen for an appropriate T cell active peptide multimer. T cell active peptide multimers are assayed by injecting a before-described composition into mice, and then testing T cells recovered from the murine lymph nodes one to three weeks after inoculation with the peptide multimer-containing composition. The measurement of activation or priming of T cells is done by T cell proliferation tests and/or interleukin-2 production (Milich et al., J. Exp. Med., 164:532, 1986).

Two types of T cell active peptides should be found. The more prevalent group of peptides prime (activate) T cells that respond in test tube assays to only the peptide and not the corresponding native HIV surface protein. The second group of peptides prime T cells to respond to both the peptide and the native HIV protein. It is this latter group of peptides that induce protective immunity in the immunized host. A plurality of strains of mice that vary in their histocompatibility genes are used for these screenings. Peptides that have a broad response in the various MHC genotypes are selected for further study in primates, and finally humans. Exemplary assay procedures are found hereinafter.

T cell active peptide multimers are also screened to identify those peptide multimers that lack B cell stimulatory activity. This is accomplished by injecting each peptide multimer into small immunocompetent animals (various strains of mice) to identify those peptides that fail to generate an antibody response to the native HIV protein to whose sequence the peptides correspond in part such as the gp120, gp41 or core proteins, for example. These animals should not produce anti-peptide antibodies that bind to (immunoreact with) the corresponding native viral protein. Those selected peptides that induce T cell activation, but do not induce an antibody response to their correlative or corresponding native protein are then assayed in baboons or other apes and monitored to confirm the lack of anti-peptide antibody production in baboon sera.

At this stage, mixtures of peptides are preferably employed in the multimer to provide a broad spectrum of coverage usually needed for an effective T cell activating composition. Peptide mixtures are then incorporated into a multimer-containing composition and assayed in a suitable animal that allows replication of the AIDS virus (e.g., chimpanzees) to test for priming of T cells. Peptides that are more active are used to immunize chimpanzees in a virus challenge study. A successful protection study prevents viremia without eliciting a significant humoral antibody response, but primes T cells for in vitro responses to the envelope antigens. The virus is then neutralized by cell mediated immunity.

A composition containing a peptide multimer in an immunologically effective amount is thus obtained that can induce a killing effective amount of cytotoxic T cells. Those cytotoxic T cells are capable of killing target cells, when contacted in vitro or in vivo with such target cells like T lymphocytes or other cells such as P815 mouse cells (when the cytotoxic T cells are from a mouse; P815 mouse cells are available from Dr. Fernando Plata of the Pasteur Institute, Paris, France) that exhibit a corresponding HIV protein or a portion of such a protein on their cell surfaces.

As described before, it is not necessary to select a peptide that completely lacks the capability to raise anti-peptide antibodies. Where such antibodies are induced, the anti-peptide antibodies must not be capable of recognizing (immunoreacting with) the native envelope proteins as measured, for example, either by immunoblotting procedures or by other immunoabsorbent (ELISA) tests. What is important in this particular response is that anti-peptide antibodies against a certain peptide sequence must not induce antibodies that bind to the infectious virus. Thus, in this case, T cell active peptides that raise low or moderate levels of anti-peptide antibodies are screened to identify those that fail to detect either intact virus preparations or viral surface proteins by immunoabsorbent tests (ELISA) and/or immunoblot procedures.

D. Methods

Methods constitute yet another aspect of the present invention.

A first method comprises the induction of T cell immunity to a preselected native HIV protein in a host animal such as a laboratory animal or a human as noted previously. Here an immunizing effective amount of a before-discussed active peptide multimer-containing composition is introduced into the host animal, and the host animal is maintained for a time period sufficient for the T cell immunity to develop. This immunization does not induce substantial production of antibodies that immunoreact with the preselected HIV protein. This immunization can be repeated or boosted from time to time as desired.

The preselected HIV native protein is a protein to which an active peptide of the multimer corresponds in sequence. As already noted, an active peptide multimer can include active peptides corresponding to different HIV proteins, and as a consequence, the above method can be used to induce T cell immunity to more than one HIV protein.

T cells from the immunized host animal can be collected and assayed for their having immunity to the preselected HIV protein using an assay such as the proliferation assay discussed hereinafter.

The immunized T cells prepared as discussed in the above method can be utilized in a method of killing target cells that exhibit an HIV protein or a portion thereof on their cell surfaces. In this method, such target cells are contacted with a killing effective amount of cytotoxic T cells that have been immunized with a before-discussed composition, as already discussed. That contact is maintained for a time period sufficient to kill the target cells.

The above method can be carried out in vitro or in vivo. For in vitro studies, immunized T cells are obtained from an immunized host animal and are admixed and contacted with the target cells in an appropriate aqueous medium such as RPMI medium. The admixture is thereafter assayed for lysis of the target cells as by the $^{51}$Cr assay discussed hereinafter.

The target cells utilized can be HIV-infected cells that express and thereby exhibit HIV proteins such as core, gp120 and gp41 on their cell surfaces. The target cells can also be cells such as spenocytes that upon admixture with a peptide used in the multimer binds that peptide to its surface and thereby exhibits a portion of an HIV protein on its surface. Further target cells include P815 mouse mastocytoma cells (ATCC TIB64 that have been further transferred to express HIV proteins, and are available from Dr. Fernando Plata of the Pasteur Institute, Paris, France, as noted before.

In an in vivo aspect of the above method, the target cells and immunized cytotoxic T cells are supplied by the immunized host animal; i.e., the host animal is infected with HIV, and HIV proteins or portions thereof are expressed on the surfaces of host cells such as $T4^+$ cells. Once a host animal such as a chimpanzee or human expresses HIV proteins on cell surfaces, the animal is usually also viremic. As a consequence, a decrease in viremia of an infected host after immunization or the absence of viremia after immunization and infection provide assays for the above method.

In still another aspect of the above method, autologous or appropriately matched heterologous cytotoxic T cells are used. For autologous cells, immunization as discussed previously can be sufficient. However, immunized T cells can be recovered as already discussed, cultured further in the presence of an immunizing peptide multimer to proliferate the cells, and then those proliferated cells can be re-introduced into the same host animal to augment the effect obtained by immunization alone.

For heterologous cells, a donor is immunized with a previously discussed composition and the donor's immunized T cells collected. Immunized T cells from an appropriately matched donor, e.g. a syngeneic donor, can be then introduced into an HIV-infected recipient as a passive immunization. Prior to the passive immunization, the matched donor cells can be proliferated as discussed above and then utilized.

The maintenance time of contact between the target cells and effector cytotoxic T cells can vary from about an hour to days, depending on several parameters, most importantly being whether the method is carried out in vivo or in vitro. For in vivo methods, the maintenance time is the lifetime of the cytotoxic T cells, which can be days to weeks. For in vitro uses, maintenance times of one to about 10 hours, and preferably about 2 to about 5 hours are generally used.

An important issue in considering the effectiveness of a peptide multimer or method of this invention is whether the cell-mediated immune system can function in a previously immunized individual when at a later time the immunized host animal is exposed to HIV which is infecting and altering the function of T4 helper cells. The research findings of Buller et al. (Nature, 328: 77, 1987) provide evidence that is consistent with the hypothesis that a T cell active peptide can invoke a cell mediated response in the absence of T4 helper cells. Their work demonstrates that cytotoxic T cell responses can be induced in mice in the absence of T helper cells; the end result was that mice being studied recovered from a viral disease without T helper cells.

Therapy for HIV-infected host animals such as people is also comtemplated by the present invention. A composition of this invention can thus be used to treat animal hosts that are already infected with HIV.

In this particular situation, it is important to consider that the target for cell mediated immunity includes not only the virus but more importantly the virus-infected cell. Such infected cells have not only viral envelope proteins on their surfaces but possibly glycosylated core proteins (gag gene products) or their higher molecular weight precursors as well (Naso et al., J. Virol., 45:1200, 1983). Therefore, T cell active peptides from the gag gene of HIV as noted before are also selected, assayed and used for their affects on virus infected cells, as discussed above.

The T helper cell-independent cytotoxic T cell response, described by Buller et al., bodes well for the use of T cell active peptide multimers in the therapy of AIDS. Such a peptide multimer or a multimer containing mixture of peptides can mount an effective cell-mediated immune response at a time when T4 cells are being infected and killed by the HIV. Since T8 cells are resistant to HIV infection, a peptide multimer can activate and prime T8 cytotoxic cells permitting a specific virus-killing response in the AIDS patient even though the virus may be infecting and altering the immune helper function of T4 cells.

Studies of Walker et al., (Nature, 328: 345, 1987) have demonstrated the presence HIV-specific cytotoxic T cells in persons infected with HIV. These cytotoxic T cells were able to kill HIV antigen-containing B lymphocytes derived from the same patient in laboratory tests. Their study showed that a monoclonal antibody specific for cytotoxic T cells was able to inhibit the cell killing activity. These results support the immunization approach described herein, and may have important implications for the use of T-cell active peptides and their multimers in the treatment of AIDS patients.

BEST MODE FOR CARRYING OUT THE INVENTION

EXAMPLE 1—Preparation of Peptides, Peptide Polymers and Peptide Micelles

Synthetic peptides of 7 to about 30 amino acid residues in length were prepared corresponding to the selected conserved domains of the core and gp160 (gp120 and gp41) molecules using the solid-phase technique of Merrifield described in J. Am. Chem. Soc. 85:2149–2154 (1963) using a modified Vega 250 automated peptide synthesizer or by the "bag" method described in Houghten, Proc. Natl. Acad. Sci, USA, 82:5131–5135 (1985). The t-butyloxycarbonyl (t-BOc) amino acid blocking groups and the hydrolysis of the peptide from the resin were carried out by hydrofluoric acid (HF) treatment at about zero degrees C for one hour. The peptide-containing mixture was then extracted with diethyl ether to remove non-peptide organic compounds and the synthesized peptides were extracted from the resin with acetic acid (25 percent w/v).

Nineteen (19) synthetic peptides have been prepared that correspond to conserved domains of the gp120 molecule and the gp41 molecule by this procedure, and are listed in TABLE 2. The synthesized peptides correspond to designated conserved domains (regions) of gp160 in HIV as shown.

TABLE 2

AMINO ACID SEQUENCE OF SYNTHETIC PEPTIDES

| PEPTIDE # | AMINO ACID SEOUENCE[1] | LOCATION IN HIV ENVELOPE[2] |
|---|---|---|
| 103 | $^{39}$EQLWVTVYYGVPV$^{51}$ | GP160-CR-1 |
| 104 | $^{45}$VYYGVPVWKEA$^{55}$ | GP160-CR-1 |
| 105 | $^{48}$GVPVWKEATTLFC$^{61}$ | GP160-CR-1 |
| 106 | $^{72}$AHKVWATHACV$^{82}$ | GP160-CR-1 |
| 107 | $^{81}$CVPTNPVPQEVV$^{92}$ | GP160-CR-1 |
| 108 | $^{92}$VLENVTENFNM$^{102}$ | GP160-CR-1 |
| 109 | $^{105}$NNMVEQMHEDII$^{116}$ | GP160-CR-1 |
| 110 | $^{109}$EQMHEDIISLWDQ$^{121}$ | GP160-CR-1 |
| 111 | $^{118}$LWDQSLKPCVKLT$^{130}$ | GP160-CR-1 |
| 112 | $^{121}$SLKPCVKLTPLC$^{133}$ | GP160-CR-1 |
| 113 | $^{204}$SVITQACSKVSFE$^{216}$ | GP160-CR-2 |
| 114 | $^{215}$FEPIPIHYCAFPGF$^{228}$ | GP160-CR-2 |
| 115 | $^{236}$KKFNGTGPCTN$^{246}$ | GP160-CR-2 |
| 116 | $^{240}$GTGPCTNVSTVQC$^{252}$ | GP160-CR-2 |
| 117 | $^{250}$VQCTHGIRPVVSTQ$^{263}$ | GP160-CR-2 |
| 61 | $^{586}$YLRDQQLLGIWGC$^{598}$ | GP160-CR-5 |
| 63 | $^{519}$FLGFLGAAGSTMGAASLTLTVQ-ARQ$^{543}$ | GP160-CR-5 |
| 65 | $^{417}$CRIKQIINMWQGVGKAMYA$^{435}$ | GP160-CR-3 |
| 67 | $^{417}$CRIKQIINMWQGVGKAMYAPP-IGGQIRC$^{444}$ | GP160-CR-3 |

[1]The N- and C-terminal amino acid residues of each peptide are numbered as to their position in the gp160 amino acid residue sequence according to Modrow etal. Virol., 61:570 (1987). A dash (-) indicates that the sequence continues on the next line.
[2]CR = Conserved Region Two types of high molecular weight (multimeric) forms of the peptides listed in TABLE 2 were prepared. The principal form of multimer was a di-cysteine (di-Cys terminated) polymer in which a plurality of peptides were linked end-to-end by disulfide bonds. These di-cysteine polymers were produced by adding a cysteine residue to the termini of each peptide during synthesis. The di-cysteine-terminated (di-Cys) peptides were then dissolved (10 mg/ml) in ammonium bicarbonate (0.1M) at room temperature (about 25 degrees C.) and stirred for about 16 hours to effect oxidation of the sulfhydryl groups to produce polymer forms of the peptides.

The second type of high molecular weight form produced was a surfactant-like micelle formed by linkage of an amino-terminal lysine-containing spacer peptide (Lys-Gly-Gly-) to the peptide sequence to form a composite polypeptide, and then coupling a $C_{12}$–$C_{18}$ fatty acid, such as palmitic acid, to both the alpha and epsilon amino groups by the method described in Hopp, Mol. Immunol. 21:13–16 (1984), which is incorporated herein by reference. The $C_{12}$–$C_{18}$ fatty acid-containing peptides produced are then extracted in acetic acid (95 percent), and utilized to form large micelles in the aqueous composition that exhibit increased immunogenicity relative to the peptides.

Di-Cys polymer multimers of all of the peptides listed in TABLE 2 were prepared. Aqueous peptide micelle multimers have been prepared of peptides designated 61, 63, 65 and 67, and are designated as peptides 62, 64, 66 and 68, respectively. Peptides designated 103 through 117 were utilized only in their di-Cys polymer multimeric forms.

The high molecular weight, multimeric forms produced correspond to multiple copies of specific regions of gp120 and gp41 in HIV. For ease of designation, the multimer forms will be designated by the peptide number from which it is composed—that is, peptide 61 refers to the di-Cys multimeric (polymeric) form of peptide 61 and peptide 66 refers to the aqueous micelle form of peptide 65, whereas peptide 103–117 refers to a polymeric multimer.

Peptides 65 and 66 correspond to the region of gp120 that binds to the cell surface $T_4$ receptor. Peptides 63 and 64 correspond to a region near the amino-terminal portion of gp41 that represents a major immunodominant epitope seen by AIDS patients' serum.

EXAMPLE 2—Anti-Peptide Antibody Response

Aqueous compositions of the multimers; i.e., the di-Cys peptide polymers and micelles produced in EXAMPLE 1 were assayed for their ability, or lack of ability to elicit an anti-peptide antibody response in BALB/c mice, an immunocompetent mouse strain.

Groups of BALB/c mice (6–8-week-old females, 3 to 5 mice/group, Charles River Laboratories) were immunized by subcutaneous (s.c.) or intraperitoneal (i.p.) injection of a peptide multimer (100 μg/injection) in complete Freund's adjuvant (CFA) (1:1 ratio). Booster injections (50 μg of peptide multimer) in incomplete Freund's adjuvant (IFA) (1:1) were given at 6 and 10 weeks after the initial immunization. Each mouse was bled from its retro-orbital plexus at two-week intervals and the serum was pooled for individual mice in each group.

An ELISA assay was performed on each serum to detect the presence of anti-peptide antibodies utilizing peroxidase-conjugated goat anti-mouse IgG (obtained from Boehringer Mannheim Biochemicals, Indianapolis, Ind.) as the second antibody). Preliminary results for peptides 61–68 are shown in TABLE 3, whereas further refined results for peptides 61, 63, 65, 67 and 103–117 are shown in TABLE 4.

It was found that the high molecular weight forms of peptides 65, 66, 67, 68, 105 to 110, 112, 114, 115 and 117 elicited high antibody titers, whereas peptides 61, 62, 63, 64, 103, 104, 111, 113 and 116 produced very low to negligible amounts of anti-peptide antibodies. Similar results were obtained for antibody responses in B6C3 F1 mice (Charles River Laboratories), another immunocompetent strain.

Some of the sera were further assayed for antibody response (reactivity) with native gp160, and the results, shown in TABLE 5, demonstrate that these peptides do not represent B cell epitopes since there was no immunoreaction with native gp160.

TABLE 3

| | | ANTIBODY RESPONSE OF VARIOUS PEPTIDES IN BALB/C MICE ELISA Titer in Bleed # | | | | | | | |
|---|---|---|---|---|---|---|---|---|---|
| Peptide # | Pre-Immune | 1 | 2 | 3 | 4 | 5 | 6 | 7 | 8 |
| 61 | 1:40 | 1:400 | 1:100 | 1:100 | 1:100 | 1:100 | 1:400 | 1:200 | 1:400 |
| 62 | 1:20 | 1:100 | 1:100 | 1:100 | 1:100 | 1:100 | 1:200 | 1:100 | 1:100 |
| 63 | 1:40 | 1:80 | 1:20 | 1:40 | 1:320 | 1:60 | 1:80 | 1:320 | 1:5120 |
| 64 | 1:20 | 1:40 | 1:40 | 1:00 | 1:40 | 1:10 | 1:40 | 1:40 | 1:40 |
| 65 | 1:40 | 1:60 | 1:600 | 1:1 × $10^4$ | 1:5 × $10^4$ | 1:5 × $10^4$ | 1:2 × $10^5$ | 1:2 × $10^5$ | 1:2 × $10^5$ |
| 66 | 1:10 | 1:160 | 1:6 × $10^3$ | 1:1 × $10^5$ | 1:1 × $10^5$ | 1:1 × $10^5$ | 1:2 × $10^4$ | 1:5 × $10^4$ | 1:5 × $10^4$ |
| 67 | 1:40 | 1:160 | 1:3 × $10^3$ | 1:2 × $10^4$ | 1:2 × $10^4$ | 1:1 × $10^5$ | 1:1 × $10^5$ | 1:1 × $10^5$ | 1:2 × $10^5$ |
| 68 | 1:80 | 1:1600 | 1:1 × $10^4$ | 1:1 × $10^4$ | 1:1 × $10^5$ | 1:1 × $10^5$ | 1:4 × $10^5$ | 1:4 × $10^5$ | 1:4 × $10^5$ |

TABLE 4

| ANTIBODY RESPONSE OF VARIOUS PEPTIDES IN BALB/C MICE | |
|---|---|
| PEPTIDE | ELISA TITER |
| #61 AA 586–598 | 1:400 |
| #63 AA 519–543 | 1:5120 |
| #65 AA 417–435 | 1:2 × $10^5$ |
| #67 AA 417–444 | 1:8 × $10^5$ |
| #103 AA 39–51 | 1:640 |
| #104 AA 45–55 | 1:2000 |
| #105 AA 48–61 | 1:5000 |
| #106 AA 72–82 | 1:4 × $10^5$ |
| #107 AA 81–92 | 1:1 × $10^5$ |
| #108 AA 92–102 | 1:1 × $10^5$ |
| #109 AA 105–116 | 1:8 × $10^5$ |
| #110 AA 109–121 | 1:6 × $10^6$ |
| #111 AA 118–130 | 1:80 |
| #112 AA 121–133 | 1:1 × $10^5$ |
| #113 AA 204–216 | 1:640 |
| #114 AA 215–228 | 1:1 × $10^6$ |
| #115 AA 236–246 | 1:4 × $10^5$ |
| #116 AA 240–252 | 1:640 |
| #117 AA 250–263 | 1:8 × $10^6$ |

TABLE 5

T AND B CELL RESPONSES IN MICE TO HIV ENVELOPE GP160 DERIVED SYNTHETIC PEPTIDE IMMUNOGENS

| | In Vitro Proliferation of PLN Cells from* | | | | Antipeptide Antibody | |
|---|---|---|---|---|---|---|
| | $B_6C_3F_1$ | | A · SW x Balb/c $F_1$ | | Reactivity to** | |
| Peptide Immunogen | Analogous Peptide | GP 160 | Analgous Peptide | GP 160 | Analogous Peptide | GP 160 |
| 61 | ++ | + | ++ | ++ | − | − |
| 63 | ++ | ++ | ++ | ++ | _+ | − |
| 65 | ++ | + | ++++ | ++ | ++ | − |
| 67 | ++ | − | ++++ | ++ | +++ | − |
| 103 | + | + | +++ | + | − | − |
| 104 | ++++ | ++ | +++ | + | ± | − |
| 105 | ++++ | +++ | + | − | ± | − |
| 106 | +++ | + | ++++ | + | ++ | − |
| 107 | ++ | ++ | + | + | + | − |
| 108 | + | + | + | − | + | − |
| 109 | ++ | ± | ± | + | +++ | − |
| 110 | ++ | − | ++ | + | ++++ | − |
| 111 | + | ++ | ± | − | − | − |
| 112 | + | + | + | + | + | − |
| 113 | ++ | + | ++ | + | − | − |
| 114 | ++ | − | ++ | + | ++++ | − |
| 115 | ++ | + | ♠ND | ND | ++ | − |
| 116 | ++ | − | ND | ND | − | − |
| 117 | +++ | − | ND | ND | ++++ | − |

*cpm values are corrected and categorized according to unrelated antigen response in vitro.

**Antibody raised in Balb/C mice, reactivity measured by ELISA and categorize according to the end point.

♠Not determined.

EXAMPLE 3—T Cell Responses

The high molecular weight, multimeric di-Cys peptide polymeric forms of the peptides described in EXAMPLE 1 were assayed for their elicitation of a T cell proliferative response by the method described in Millich et al., J. Immunol. 134:4194–4203 (1985), incorporated herein by reference.

Mice (3 or 5 mice/group) were injected in the right hind footpad with a peptide polymer (100 $\mu$g/injection) in complete Freund's adjuvant (1:1). Peptides 61, 63, 65 and 67 were injected into B6C3 F1 mice (H-$2^{kxb}$ (Charles River Laboratories) and A.SWxBALB/C F1 mice (H-$2^{sxd}$) (Jackson Labs, Bar Harbor, Me.). Draining popliteal lymph node (PLN) cells were harvested after ten (10) days, and cultured ($2\times10^5$ cells/well) in 96-well microtiter plates in 0.2 ml of Click's medium (Click et al., Cellular Immunol. 3:264–276 (1972)] containing various concentrations of synthetic peptide, gp160, an unrelated proteinaceous material or medium alone, for 96 hours at 37 degrees C. in a humidified atmosphere of 5 percent $CO_2$. During the final 16–18 hours of culturing, $^3$H-thymidine ($^3$H-TdR) (1 $\mu$Ci/well, 6–7 Ci/mmole, ICN Radiochemicals) was added. The cells were harvested onto filter strips and $^3$H-TDR incorporation was monitored. The data are presented in FIGS. 1, 2, 3, 4 and 5.

FIG. 1 illustrates the results for peptides 61, 63, 65, 67 in BALB/c mice, and those results are expressed as a stimulation index (SI) representing the fold increase in radioactivity counts in the presence of antigen compared to background values where no antigen was added. The SI values with the different peptides were compared to that obtained with tuberculin purified protein derivative (PPD) as a positive control antigen.

FIGS. 2–5 illustrate the peptide-specific $^3$H-TdR incorporation for T cell responses (delta cpm) in mice with differing major histocompatibility (MHC) haplotypes, B6C3 F1 (C57B1/6xC$^3$H/HcJ) mice (FIGS. 2 and 4) and (A.SWxBALB/c) F1 mice (FIGS. 3 and 5), for all of the synthetic peptides. The $^3$H-TdR incorporation values represent the difference between the radioactivity values obtained in wells containing antigen and in control wells without added antigen. The non-specific proliferation of PLN cells was determined by including an unrelated peptide in the assays, shown as a horizontal bar for each peptide.

All of the assayed peptides exhibited good T cell proliferative responses in B6C3 F1 mice, whereas all of the assayed peptides, except peptides 105, 107, 109 and 111, exhibited good T cell proliferative responses in SWxBALB/c F1 mice.

It was demonstrated by the results above and those described in EXAMPLE 2 that peptides 61, 63, 103, 104 and 113 do not stimulate anti-peptide antibody production but are very good immunogens, in their disulfide (di-Cys) polymeric form, for eliciting a strong T cell response directed against both the corresponding peptide and the native HIV envelope protein gp160.

Figure 6A:
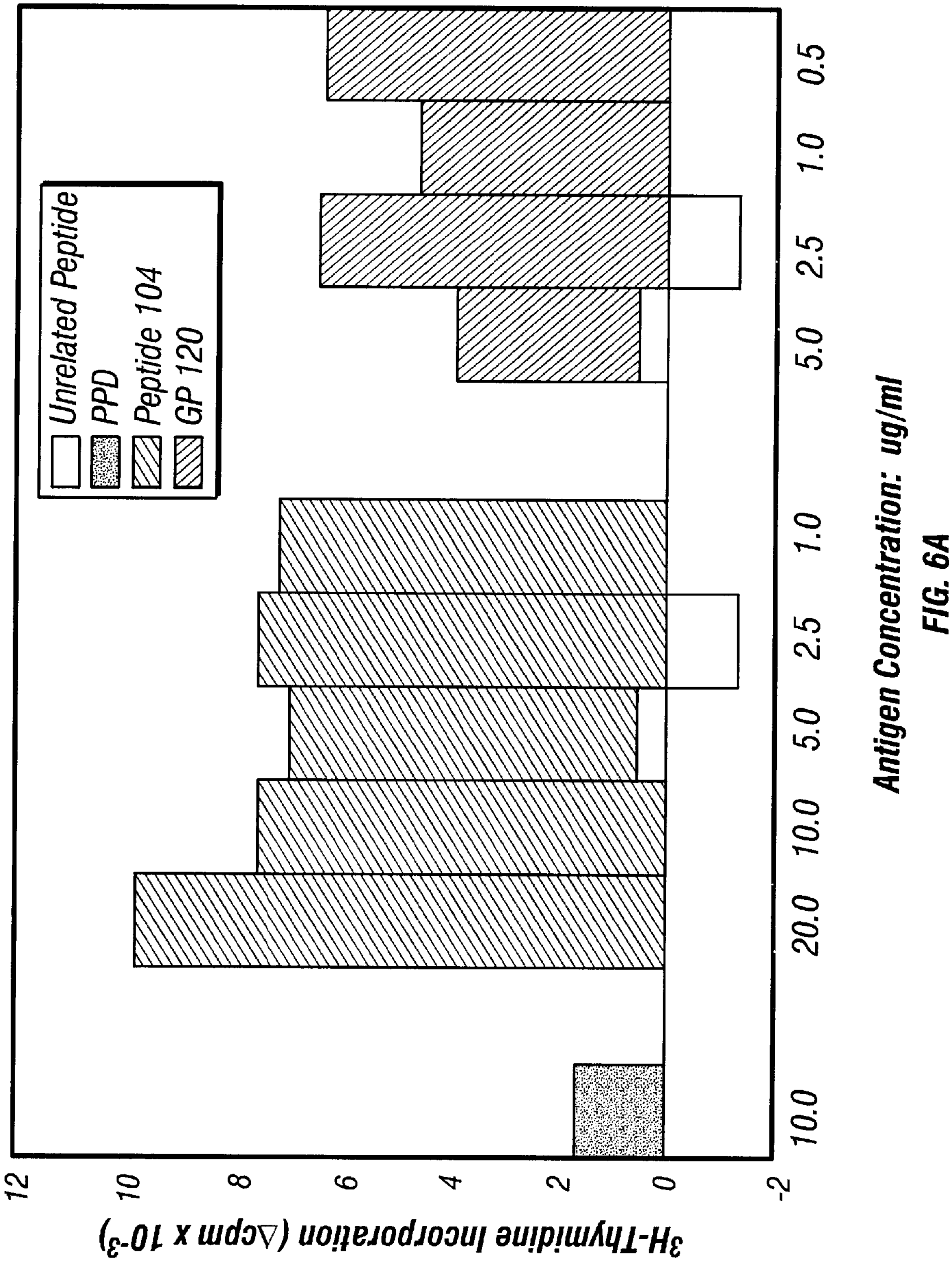
FIGS. 6A–6B contains two panels of graphs that illustrate B6C3 F1 mouse PLN cell proliferation by $^{3}$H-TdR incorporation as described before using varying concentrations of peptide multimer and gp120 as antigens. Panel A illustrates results for a peptide multimer polymer prepared from peptides 104, whereas Panel B illustrates results using a multimer prepared from peptide 106. PPD and unrelated peptide were used as controls. A further discussion relating to FIGS. 6–8 is found hereinafter.
Figure 6B:
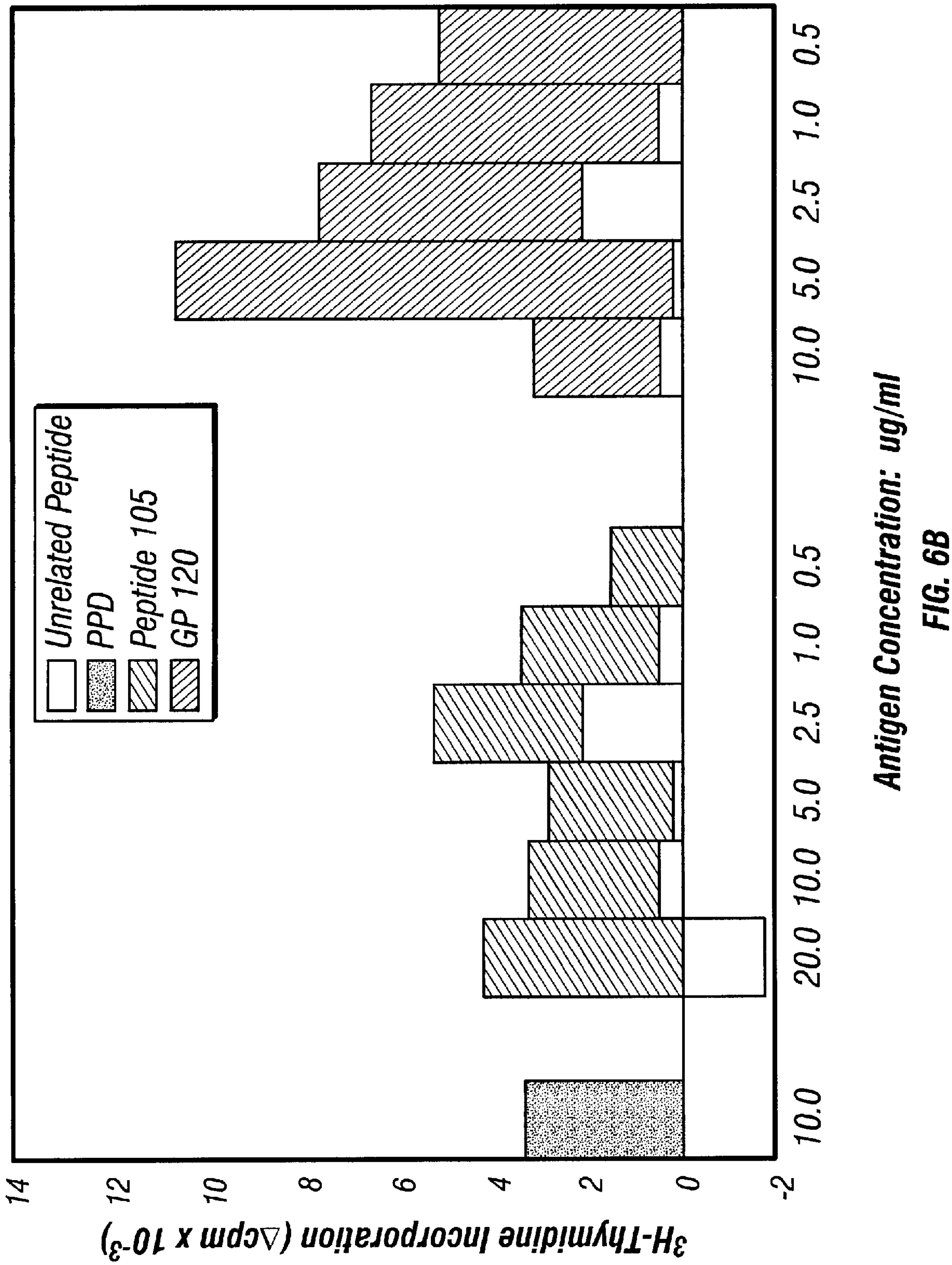
Figure 7A:
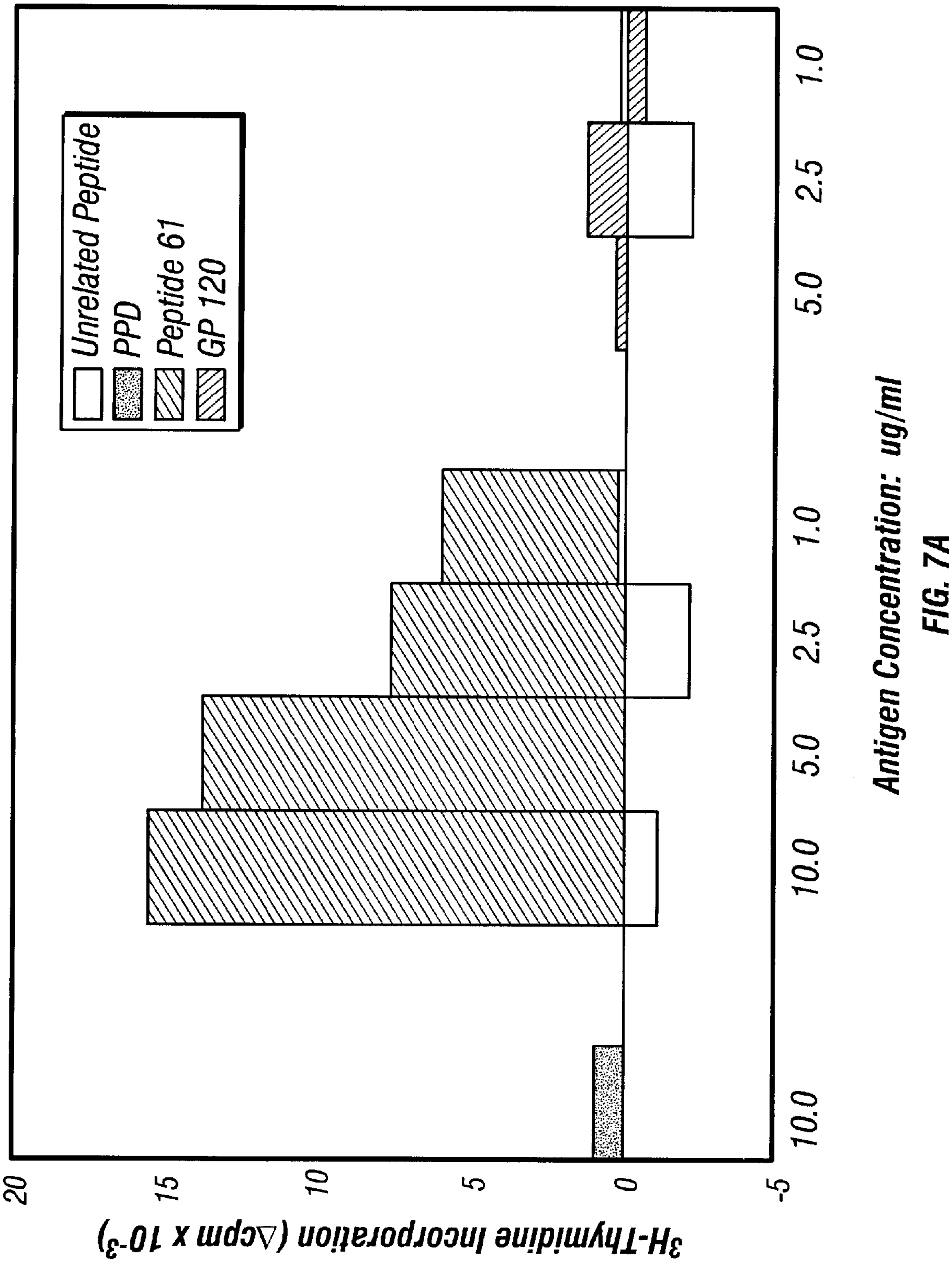
FIGS. 7A–7B contain two panels, and illustrates studies of PLN cell proliferation from B6C3 F1 mice using various concentrations of gp160 and peptide multimer polymers prepared from peptides 61 (Panel A) and 63 (Panel B) as antigens, with PPD, and an unrelated peptide as controls.
Figure 7B:
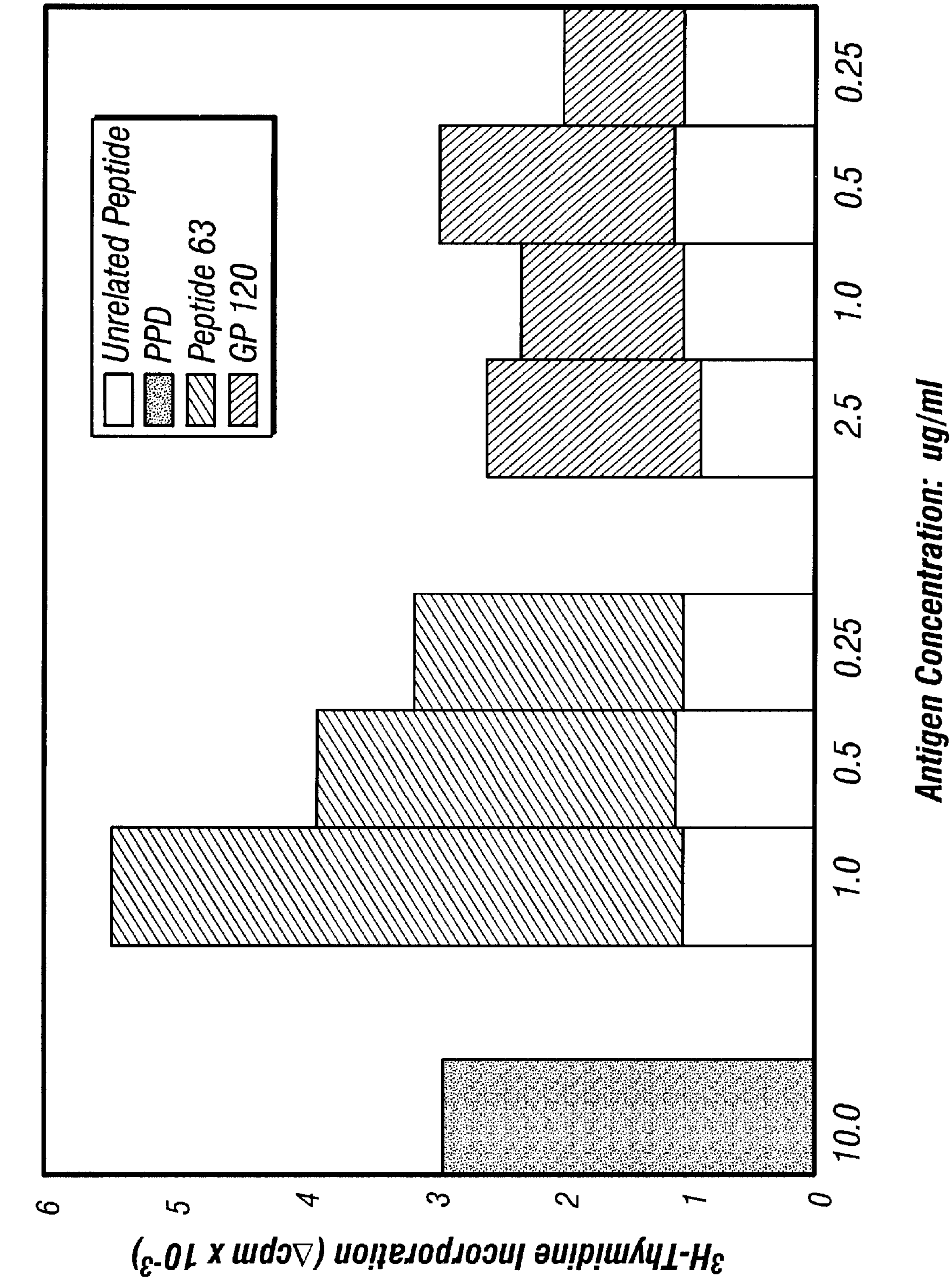
Figure 8A:
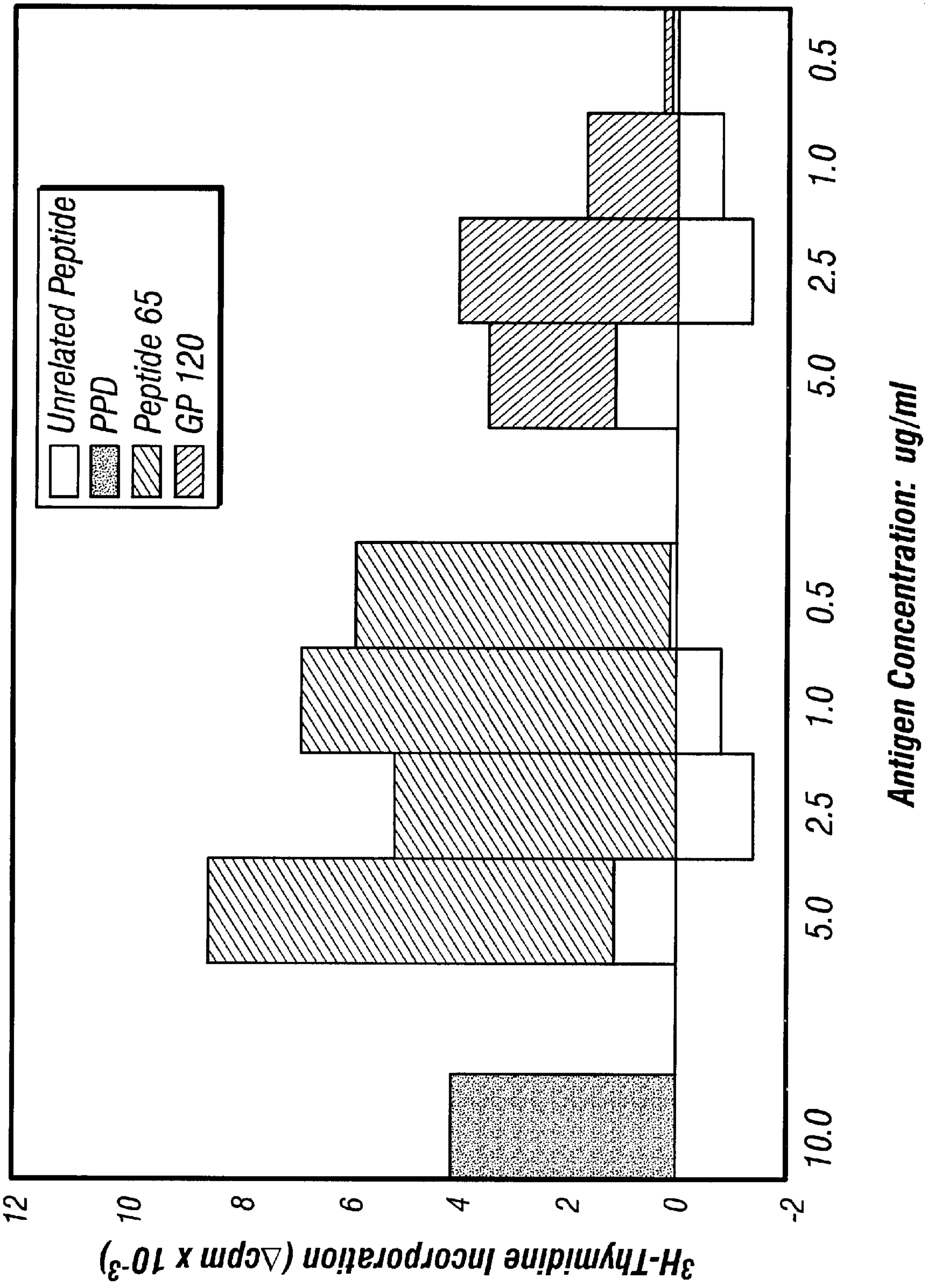
FIGS. 8A–8B contain two panels, and illustrates studies of PLN cell proliferation from B6C3 F1 mice using various concentrations of gp120 and peptide multimer polymers prepared from peptides 65 (Panel A) and 111 (Panel B) as antigens, with PPD and an unrelated peptide as controls.
Figure 8B:
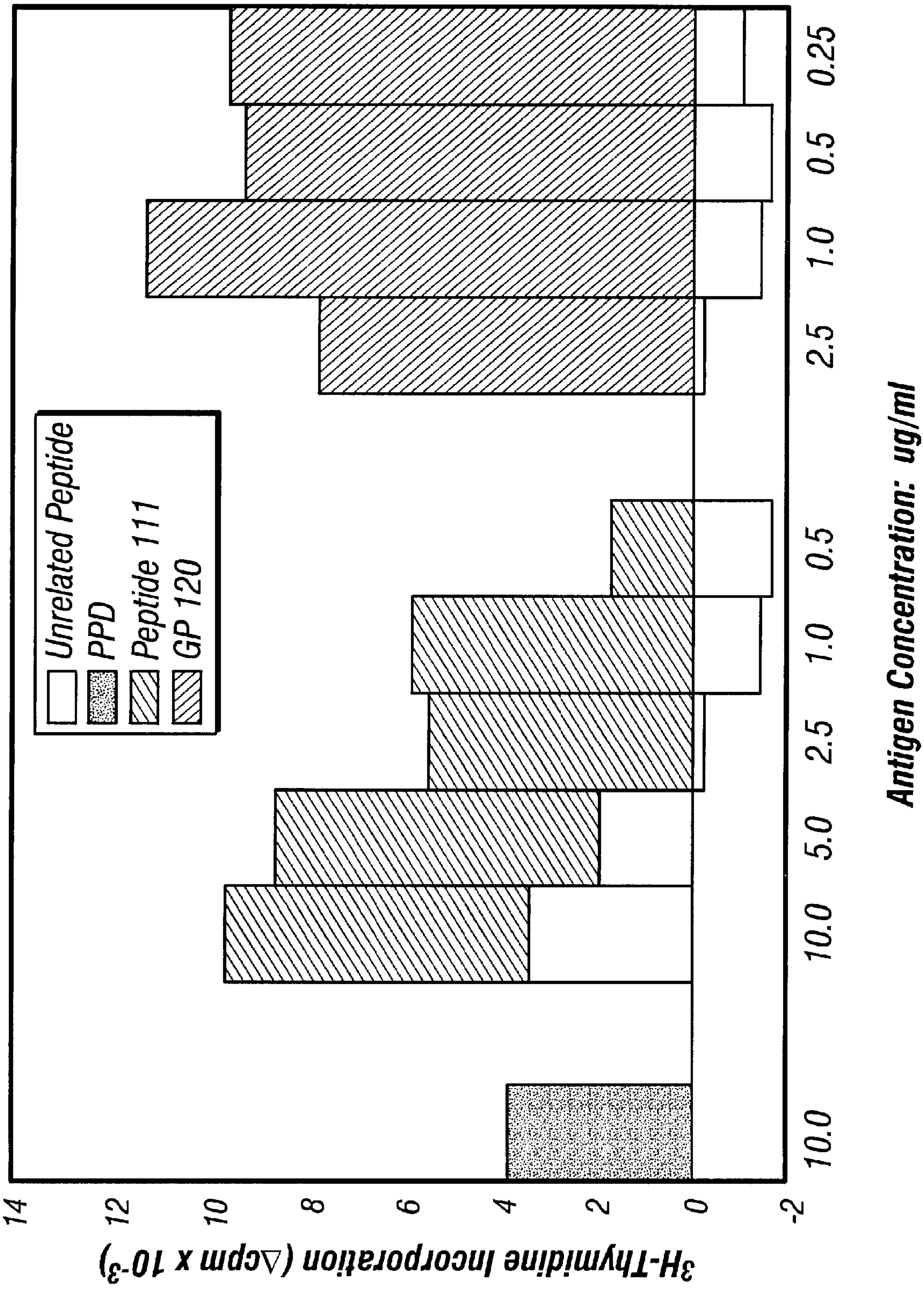

T cell proliferation measured by $^3$H-TdR incorporation, was also similarly assayed as a function of the T cell antigen concentration, using various amounts of native gp120 or gp160 as one control, and PPD as another control. PLN from B6C3 F1 mice were used in these studies. The results for peptides 104 and 105 versus gp120 are shown in FIGS. 6A and 6B, respectively; those for peptides 61 and 63 versus gp160 are shown in FIGS. 7A and 7B, respectively; and those for peptides 65 and 111 versus gp120 are shown in FIGS. 8A and 8B, respectively.

EXAMPLE 4—Induction of HIV-Specific Cytotoxic T Lymphocytes

Groups of 3 to 5 syngeneic female mice (6 to 8 weeks of age) are immunized by injection in an appropriate site with an aqueous composition containing an immunizing (cytotoxic T cell stimulating) amount of either of the before-discussed multimers, in a mixture with CFA (1:1). Ten (10) days after immunization, draining PLN cells and spleen lymphocytes are obtained and restimulated in vitro by culturing for six (6) days with the same synthetic peptide as immunogen.

The presence of cytotoxic T lymphocytes (CTL) is determined by a 6-hour $^{51}$Cr release assay as follows. The PLN and spleen cells are maintained for six days at 37 degrees C. in RPMI 1640 medium containing 10 percent fetal calf serum (FCS) together with different concentrations of the appropriate test peptide multimer from the aqueous composition. These cells are designated as the effector cells, and are H-$2^d$.

Target cells (phytohemagglutinin-stimulated (PHA) blasts of syngeneic mouse spleen cells or P815 mouse cells expressing a corresponding HIV protein] ($1\times10^6$/assay sample) are washed with serum-free RPMI 1640 medium three times and then admixed, contacted and maintained (incubated) at 37 degrees C. for about 1.5 to about 3 hours together with various concentrations of the test peptide and 300 $\mu$Ci of sodium chromate (specific activity 200–500 $\mu$Ci/mg of Cr, New England Nuclear, Boston, Mass.). The target cells samples are subsequently washed with RPMI 1640 medium containing 10 percent FCS and the appropriate peptide, and resuspended in RPMI 1640 with 10 percent FCS ($2\times10^5$ cells/ml) and different concentrations of peptide. A 100 $\mu$l aliquot of each cell suspension is added to a well of a 96-well-U-bottom microtiter plate.

A 100 $\mu$l aliquot of the appropriate effector cell suspension is added to each well and a twofold serial dilution made to obtain different effector-to-target cell (E:T) ratios. Control wells receive 0.1 ml of RPMI medium with 10 percent FCS alone in the absence of effector cells to obtain a value for spontaneous $^{51}$Cr release, and receive 0.1 ml of 5 percent Triton X-100 detergent to obtain a value for total $^{51}$Cr release.

The plates are incubated at 37 degrees C. for about 3 to about 4 hours, following which 100 $\mu$l of supernatant from each well is monitored in a gamma counter to determine $^{51}$Cr release. The percent cytotoxicity is calculated as $$\frac{(\text{Effector Cell} - \text{Stimulated Release}) - (\text{Spontaneous Release})}{\text{Total Release} - \text{Spontaneous Release}} \times 100$$

Changes may be made in the construction, operation and arrangement of the various parts, elements, steps and procedures described herein without departing from the concept and scope of the invention as defined in the following claims.

What is claimed is:

1. An isolated peptide of from 7 to about 30 acid residues comprising one or more of the following amino acid residues of gp120 within its structure: $AA^{39-51}$; $AA^{45-55}$; $AA^{48-61}$; $AA^{72-82}$; $AA^{81-92}$; $AA^{92-102}$; $AA^{105-116}$; $AA^{118-130}$; $AA^{204-216}$; $AA^{215-228}$; $AA^{240-252}$; $AA^{586-598}$; $AA^{519-543}$; or $AA^{417-435}$.

2. The peptide according to claim 1 wherein said peptide includes within its structure an amino acid residue sequence, from left to right and in the direction from amino-terminus to carboxy-terminus, represented by a formula selected from the group consisting of:

—YLRDQQLLGIWGC—,
—FLGFLGAAGSTMGAASLTLTVARQ—,
—EQLWVTVYYGVPV—,
—VYYGVPVWKEA—,
—SVITQACSKVSFE—, and
—GVPVWKEATTLFC—.

3. The peptide according to claim 1 wherein said peptide includes within its structure an amino acid residue sequence, from left to right and in the direction from amino-terminus to carboxy-terminus, represented by a formula selected from the group consisting of:

YLRDQQLLGIWGC,
FLGFLGAAGSTMGAASLTLTVARQ,
EQLWVTVYYGVPV,
VYYGVPVWKEA
SVITQACSKVSFE,
GVPVWKEATTLFC,
AHKVWATHACV,
CVPTNPVPQEVV,
FEPIPIHYCAFPGF,
EGCRQIL,
ELRSLYNTVAT,
VIPMFSALSEG,
AMQMLKET,
YVDREYKT,
KTILKALGPA, and
EMMTACQGV.

4. The peptide of claim 1, wherein said peptide includes within its structure an amino acid sequence of —EQLWVTVYYGVPV—.

5. The peptide of claim 1, wherein said peptide includes within its structure an amino acid sequence of —VYYGVPVWKEA—.

6. The peptide of claim 1, wherein said peptide includes within its structure an amino acid sequence of —GVPVWKEATTLFC—.

7. The peptide of claim 1, wherein said peptide includes within its structure an amino acid sequence of —AHKVWATHACV—.

8. The peptide of claim 1, wherein said peptide includes within its structure an amino acid sequence of —CVPTNPVPQEVV—.

9. The peptide of claim 1, wherein said peptide includes within its structure an amino acid sequence of —VLENVTENFNM—.

10. The peptide of claim 1, wherein said peptide includes within its structure an amino acid sequence of —NNMVEQMHEDII—.

11. The peptide of claim 1, wherein said peptide includes within its structure an amino acid sequence of —LWDQSLKPCVKLT—.

12. The peptide of claim 1, wherein said peptide includes within its structure an amino acid sequence of —SVITQACSKVSFE—.

13. The peptide of claim 1, wherein said peptide includes within its structure an amino acid sequence of —FEPIPIHYCAFPGF—.

14. The peptide of claim 1, wherein said peptide includes within its structure an amino acid sequence of —GTGPCTNVSTVQC—.

15. The peptide of claim 1, wherein said peptide includes within its structure an amino acid sequence of —VQCTHGIRPVVSTQ—.

16. The peptide of claim 1, wherein said peptide includes within its structure an amino acid sequence of —YLRDQQLLGIWGC—.

17. The peptide of claim 1, wherein said peptide includes within its structure an amino acid sequence of —FLGFLGAAGSTMGAASLTLTVOARO—.

18. The peptide of claim 1, wherein said peptide includes within its structure an amino acid sequence of —CRIKQIINMWQGVGKAMYA—.

* * * * *

UNITED STATES PATENT AND TRADEMARK OFFICE

CERTIFICATE OF CORRECTION

PATENT NO. : 6,265,539 B1
DATED : July 24, 2001
INVENTOR(S) : Raplh B. Arlinghaus It is certified that error appears in the above-identified patent and that said Letters Patent is hereby corrected as shown below:

Title page,
Item [73], Assignee, delete "Austine" and replace with -- Austin --.
Item [56], References Cited, in U.S. Patent No. 5,030,449, delete "530/526" and replace with -- 424/88 --.

Column 34,
Line 10, delete "OARO" and replace with -- QARQ --.

Signed and Sealed this

Eleventh Day of June, 2002

*Attest:*

JAMES E. ROGAN

*Attesting Officer*

*Director of the United States Patent and Trademark Office*